United States Patent
Im et al.

(10) Patent No.: US 12,163,084 B2
(45) Date of Patent: *Dec. 10, 2024

(54) MONOAZO DICHROIC DYE COMPOUND, POLARIZING PLATE COMPOSITION COMPRISING SAME, POLARIZING PLATE FORMED THEREFROM, AND OPTICAL DEVICE COMPRISING SAME

(71) Applicant: LG CHEM, LTD., Seoul (KR)

(72) Inventors: Seo-Young Im, Daejeon (KR); Duy Hieu Le, Daejeon (KR); Ho-Yong Lee, Daejeon (KR); Jae-Myeng Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/026,766

(22) PCT Filed: Jul. 15, 2021

(86) PCT No.: PCT/KR2021/009137
§ 371 (c)(1),
(2) Date: Mar. 16, 2023

(87) PCT Pub. No.: WO2022/139099
PCT Pub. Date: Jun. 30, 2022

(65) Prior Publication Data
US 2023/0340331 A1    Oct. 26, 2023

(30) Foreign Application Priority Data
Dec. 23, 2020 (KR) .................. 10-2020-0181624

(51) Int. Cl.
| | |
|---|---|
| *G02F 1/1333* | (2006.01) |
| *C07D 493/04* | (2006.01) |
| *C07D 495/04* | (2006.01) |
| *C07D 513/04* | (2006.01) |
| *C09B 29/36* | (2006.01) |
| *C09K 19/60* | (2006.01) |
| *G02B 5/30* | (2006.01) |

(52) U.S. Cl.
CPC .......... *C09K 19/601* (2013.01); *C07D 493/04* (2013.01); *C07D 495/04* (2013.01); *C07D 513/04* (2013.01); *C09B 29/3691* (2013.01); *G02B 5/3016* (2013.01)

(58) Field of Classification Search
CPC ........ C09K 19/24; C09K 19/32; C09K 19/34; C09K 19/3441; C09K 19/40; C09K 19/601; G02F 1/1333; G02B 5/3016; C07D 493/04; C07D 495/04; C07D 513/04; C09B 29/3691

See application file for complete search history.

(56) References Cited

U.S. PATENT DOCUMENTS

| | | | |
|---|---|---|---|
| 4,843,153 A | 6/1989 | Eilingsfeld et al. | |
| 5,738,806 A | * 4/1998 | Beckmann | .............. C08F 20/38 252/582 |
| 2011/0074491 A1 | 3/2011 | Yofu et al. | |
| 2011/0075076 A1 | 3/2011 | Nishiguchi et al. | |
| 2013/0070899 A1 | 3/2013 | Morishima et al. | |
| 2023/0340331 A1* | 10/2023 | Im | ......................... C07D 495/04 |
| 2023/0357638 A1* | 11/2023 | Im | ....................... C09B 29/0003 |

FOREIGN PATENT DOCUMENTS

| | | |
|---|---|---|
| CN | 102822704 A | 12/2012 |
| JP | 2002-189295 A | 7/2002 |
| JP | 2011-213841 A | 10/2011 |
| JP | 2013-139521 A | 7/2013 |
| JP | 2017-88784 A | 5/2017 |
| JP | 2018-53167 A | 4/2018 |
| JP | 2018-124467 A | 8/2018 |
| JP | 2019-211770 A | 12/2019 |
| KR | 10-2011-0015562 A | 2/2011 |
| KR | 10-2011-0035941 A | 4/2011 |
| KR | 10-2019-0078428 A | 7/2019 |

OTHER PUBLICATIONS

Manuela, et al. (2016), "Synthesis, Fluorescence and Two-Photon Absorption Properties of Push-Pull 5-Arylthieno[3,2-b]Thienothiophene Derivatives," European Journal of Organic Chemistry, pp. 5263-5273.

* cited by examiner

*Primary Examiner* — Geraldina Visconti
(74) *Attorney, Agent, or Firm* — Bryan Cave Leighton Paisner LLP

(57) ABSTRACT

Disclosed is a mono-azo dichroic dye compound represented by the following Chemical Formula 1, a composition for polarizing plate, a polarizing plate, and an optical device.

[Chemical Formula 1]

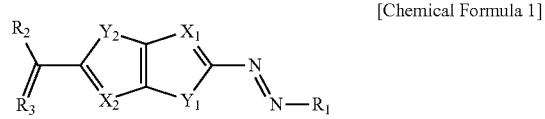

In Chemical Formula 1, $R_3$ represents a substituted or non-substituted heterocyclic group having 1-20 carbon atoms. The mono-azo dichroic dye compound shows excellent dichroic properties, and has excellent heat resistance and photo-resistance, and thus may be used advantageously for a dye-based polarizing plate.

15 Claims, No Drawings

MONOAZO DICHROIC DYE COMPOUND, POLARIZING PLATE COMPOSITION COMPRISING SAME, POLARIZING PLATE FORMED THEREFROM, AND OPTICAL DEVICE COMPRISING SAME

CROSS-REFERENCE TO RELATED APPLICATIONS

This application is a National Phase entry pursuant to 35 U.S.C. § 371 of International Application No. PCT/KR2021/009137, filed on Jul. 15, 2021, and claims the benefit of and priority to Korean Patent Application No. 10-2020-0181624, filed on Dec. 23, 2020, the disclosures of which are incorporated by reference in their entirety for all purposes as if fully set forth herein.

TECHNICAL FIELD

The present disclosure relates to a dichroic dye compound combined with a liquid crystal compound to form a polarizing plate, a composition for a polarizing plate including the same, a polarizing plate formed therefrom, and an optical device including the same.

BACKGROUND

Optical devices, such as a liquid crystal display or an organic light emitting diode, uses a polarizing plate to control optical activity or birefringence property, or to prevent reflection of external light.

Polarizing plates used typically include a polarizing plate including iodine as a polarizing substance, adsorbed to and aligned on a polarizing plate substrate made of polyvinyl alcohol or a derivative thereof, or a polarizing plate formed by combining a dichroic dye with a liquid crystal compound.

An iodine-based polarizing plate using iodine as a polarizing plate (polarizing element) shows excellent initial polarizing property in the visible light region but shows significantly low polarizing property in the near ultraviolet ray region. Moreover, such a polarizing plate is liable to water and heat, and shows a problem in terms of durability, when being used under a high-temperature and high-humidity condition for a long time.

A dye-based polarizing plate using a dichroic dye as a polarizing substance generally has higher durability under a high-temperature and high-humidity condition, as compared to an iodine-based polarizing plate, and thus is used for a part requiring high heat resistance and durability, such as a car dashboard, an airplane, a liquid crystal projector, etc. However, such a polarizing plate also has limited heat resistance and durability depending on dye and polymer materials used therefor.

Meanwhile, a bis-azo dye compound used as a polarizing substance for a dye-based polarizing plate requires a complicated synthesis process and shows a low yield undesirably.

The background description provided herein is for the purpose of generally presenting context of the disclosure. Unless otherwise indicated herein, the materials described in this section are not prior art to the claims in this application and are not admitted to be prior art, or suggestions of the prior art, by inclusion in this section.

DISCLOSURE

Technical Problem

The present disclosure is directed to providing a mono-azo dichroic dye compound which has excellent dichroic properties and high heat resistance and photo-resistance, and thus may be used advantageously for a dye-based polarizing plate.

The present disclosure is also directed to providing a composition for a polarizing plate which has the above-mentioned characteristics, and a polarizing plate formed therefrom.

In addition, the present disclosure is directed to providing an optical device including the polarizing plate having the above-mentioned characteristics.

Technical Solution

According to the first embodiment of the present disclosure, there is provided a mono-azo dichroic dye compound represented by the following Chemical Formula 1:

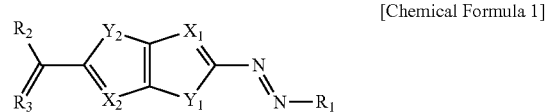

[Chemical Formula 1]

wherein each of $R_1$ represents any one selected from the group consisting of: any one selected from substituted or non-substituted aryl groups having 1-20 carbon atoms, substituted or non-substituted heteroaryl groups having 1-20 carbon atoms, and substituted or non-substituted alkyl groups having 1-20 carbon atoms; $NR_4OH$; $NHR_5$; $NR_6$; $OR_7$; $COOR_8$; $OCOR_9$; $SR_{10}$; halogen groups; OH; CN; COOH; $PO_3$; $SO_3$; and $NO_2$ (wherein each of $R_4$-$R_{10}$ has 1-20 carbon atoms, and independently represents any one selected from the group consisting of: any one selected from H, alkoxy groups and alkoxyalkyl groups; any one of halogen atoms and halogen-containing alkyl groups; and any one selected from heterocyclic groups and aryl groups, non-substituted or substituted with at least one selected from the group consisting of alkoxy groups, alkoxyalkyl groups, halogens and alkyl groups);

$R_2$ represents any one selected from the group consisting of: H; any one selected from substituted or non-substituted aryl groups having 1-20 carbon atoms, substituted or non-substituted heteroaryl groups having 1-20 carbon atoms, and substituted or non-substituted alkyl groups having 1-20 carbon atoms; $NR_4OH$; $NHR_5$; $NR_6$; $OR_7$; $COOR_8$; $OCOR_9$; $SR_{10}$; halogen groups; OH; CN; COOH; $PO_3$; $SO_3$; and $NO_2$ (wherein each of $R_4$-$R_{10}$ has 1-20 carbon atoms, and independently represents any one selected from the group consisting of: any one selected from H, alkoxy groups and alkoxyalkyl groups; any one of halogen atoms and halogen-containing alkyl groups; and any one selected from heterocyclic groups and aryl groups, non-substituted or substituted with at least one selected from the group consisting of alkoxy groups, alkoxyalkyl groups, halogens and alkyl groups);

each of $X_1$ and $X_2$ independently represents any one selected from the group consisting of N, S, O and C;

each of $Y_1$ and $Y_2$ independently represents any one selected from the group consisting of C, S, O and N; and $R_3$ represents a substituted or non-substituted heterocyclic group having 1-20 carbon atoms.

According to the second embodiment of the present disclosure, there is provided the mono-azo dichroic dye compound as defined in the first embodiment, wherein $R_1$ represents any one selected from the group consisting of CN, OH, $NHR_5$, $NR_6$, $OR_7$ and $COOR_8$, and $R_2$ represents any one selected from the group consisting of H, CN, OH, NHR$_5$, NR$_6$, OR$_7$ and COOR$_8$.

Particularly, R$_1$ may be any one selected from the group consisting of NHR$_5$, NR$_6$, OR$_7$ and COOR$_8$, and R$_2$ represents any one selected from the group consisting of H, NHR$_5$, NR$_6$, OR$_7$ and COOR$_8$.

More particularly, R$_1$ may be NR$_6$ or OR$_7$, and R$_2$ may be H, OR$_7$ or COOR$_8$.

According to the third embodiment of the present disclosure, there is provided the mono-azo dichroic dye compound as defined in the first or the second embodiment, wherein each of X$_1$ and X$_2$ is independently selected from N and C.

According to the fourth embodiment of the present disclosure, there is provided the mono-azo dichroic dye compound as defined in any one of the first to the third embodiments, wherein each of Y$_1$ and Y$_2$ is independently selected from S and O.

According to the fifth embodiment of the present disclosure, there is provided the mono-azo dichroic dye compound as defined in any one of the first to the fourth embodiments, wherein R$_3$ represents any one selected from the group consisting of: barbituric acid; hydantoin; 3-thiohydantoin; 1,3-indanedione; and dihydrouracil, non-substituted or substituted with at least one selected from the group consisting of alkyl, arylalkyl, aryl, halogen, alkoxy, alkoxyalkyl, alkoxyaryl, nitro, cyano, carboxyl and amide groups. Particularly, R$_3$ may represent any one selected from the group consisting of: barbituric acid; hydantoin; and 3-thiohydantoin, non-substituted or substituted with at least one selected from the group consisting of alkyl, arylalkyl and aryl groups.

In another aspect of the present disclosure, there are provided a composition for a polarizing plate including the mono-azo dichroic dye compound as defined in any one of the first to the fifth embodiments in combination with a liquid crystal compound, and a polarizing plate formed by curing the composition. The polarizing plate may have a dichroic ratio of 19-25, a heat resistance (Δ intensity) of 6% or less, and a photo-resistance (Δ intensity) of 3% or less.

In still another aspect of the present disclosure, there is provided an optical device including the polarizing plate.

Advantageous Effects

The dichroic dye compound according to the present disclosure is a mono-azo typed dichroic dye compound represented by Chemical Formula 1, shows excellent dichroic properties, and has excellent heat resistance and photo-resistance. Therefore, the dichroic dye compound shows high durability, even when being prepared or used under a severe condition.

In addition, the mono-azo typed dichroic dye compound is synthesized more easily with a higher yield, as compared to a bis-azo typed dichroic dye compound.

DETAILED DESCRIPTION

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

The mono-azo dichroic dye compound according to the present disclosure is represented by the following Chemical Formula 1, and is a mono-azo type compound having an azo group only at one side.

[Chemical Formula 1]

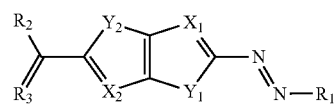

wherein R$_1$ represents any one selected from the group consisting of: any one selected from substituted or non-substituted aryl groups having 1-20 carbon atoms, substituted or non-substituted heteroaryl groups having 1-20 carbon atoms, and substituted or non-substituted alkyl groups having 1-20 carbon atoms; NR$_4$OH; NHR$_5$; NR$_6$; OR$_7$; COOR$_8$; OCOR$_9$; SR$_{10}$; halogen groups; OH; CN; COOH; PO$_3$; SO$_3$; and NO$_2$ (wherein each of R$_4$-R$_{10}$ has 1-20 carbon atoms, and independently represents any one selected from the group consisting of: any one selected from H, alkoxy groups and alkoxyalkyl groups; any one of halogen atoms and halogen-containing alkyl groups; and any one selected from heterocyclic groups and aryl groups, non-substituted or substituted with at least one selected from the group consisting of alkoxy groups, alkoxyalkyl groups, halogens and alkyl groups);

R$_2$ represents any one selected from the group consisting of: H; any one selected from substituted or non-substituted aryl groups having 1-20 carbon atoms, substituted or non-substituted heteroaryl groups having 1-20 carbon atoms, and substituted or non-substituted alkyl groups having 1-20 carbon atoms; NR$_4$OH; NHR$_5$; NR$_6$; OR$_7$; COOR$_8$; OCOR$_9$; SR$_{10}$; halogen groups; OH; CN; COOH; PO$_3$; SO$_3$; and NO$_2$ (wherein each of R$_4$-R$_{10}$ has 1-20 carbon atoms, and independently represents any one selected from the group consisting of: any one selected from H, alkoxy groups and alkoxyalkyl groups; any one of halogen atoms and halogen-containing alkyl groups; and any one selected from heterocyclic groups and aryl groups, non-substituted or substituted with at least one selected from the group consisting of alkoxy groups, alkoxyalkyl groups, halogens and alkyl groups);

each of X$_1$ and X$_2$ independently represents any one selected from the group consisting of N, S, O and C;

each of Y$_1$ and Y$_2$ independently represents any one selected from the group consisting of C, S, O and N; and R$_3$ represents a substituted or non-substituted heterocyclic group having 1-20 carbon atoms.

As described above, it is known that a bis-azo typed dichroic dye compound requires a complicated synthesis process and shows a significantly low yield. The dichroic dye compound according to the present disclosure is a mono-azo typed compound, and thus is obtained through a relatively simple synthesis process with an improved yield. In addition, even though the dichroic compound is a mono-azo typed compound, it shows excellent dichroic properties, and has high heat resistance and photo-resistance.

[R$_1$ and R$_2$ in Chemical Formula 1]

R$_1$ represents any one selected from the group consisting of: any one selected from substituted or non-substituted aryl groups having 1-20 carbon atoms, substituted or non-substituted heteroaryl groups having 1-20 carbon atoms, and substituted or non-substituted alkyl groups having 1-20 carbon atoms; NR$_4$OH; NHR$_5$; NR$_6$; OR$_7$; COOR$_8$; OCOR$_9$; SR$_{10}$ halogen groups; OH; CN; COOH; PO$_3$; SO$_3$;

and $NO_2$ (wherein each of $R_4$-$R_{10}$ has 1-20 carbon atoms, and independently represents any one selected from the group consisting of: any one selected from H, alkoxy groups and alkoxyalkyl groups; any one of halogen atoms and halogen-containing alkyl groups; and any one selected from heterocyclic groups and aryl groups, non-substituted or substituted with at least one selected from the group consisting of alkoxy groups, alkoxyalkyl groups, halogens and alkyl groups).

$R_2$ independently represents any one selected from the group consisting of: H; any one selected from substituted or non-substituted aryl groups having 1-20 carbon atoms, substituted or non-substituted heteroaryl groups having 1-20 carbon atoms, and substituted or non-substituted alkyl groups having 1-20 carbon atoms; $NR_4OH$; $NHR_5$; $NR_6$; $OR_7$; $COOR_8$; $OCOR_9$; $SR_{10}$; halogen groups; OH; CN; COOH; $PO_3$; $SO_3$; and $NO_2$ (wherein each of $R_4$-$R_{10}$ has 1-20 carbon atoms, and independently represents any one selected from the group consisting of: any one selected from H, alkoxy groups and alkoxyalkyl groups; any one of halogen atoms and halogen-containing alkyl groups; and any one selected from heterocyclic groups and aryl groups, non-substituted or substituted with at least one selected from the group consisting of alkoxy groups, alkoxyalkyl groups, halogens and alkyl groups).

In the expression 'substituted or non-substituted aryl groups having 1-20 carbon atoms, substituted or non-substituted heteroaryl groups having 1-20 carbon atoms, and substituted or non-substituted alkyl groups having 1-20 carbon atoms' used to define $R_1$ and $R_2$, the term 'substituted' refers to substitution of an aryl, heteroaryl or alkyl groups with at least one substituent selected from the group consisting of alkoxy, alkoxyalkyl, halogen and alkyl groups, or the like.

Particularly, $R_1$ represents any one selected from the group consisting of CN, OH, $NHR_5$, $NR_6$, $OR_7$ and $COOR_8$, and $R_2$ represents any one selected from the group consisting of H, CN, OH, $NHR_5$, $NR_6$, $OR_7$ and $COOR_8$.

More particularly, $R_1$ may be any one selected from the group consisting of $NHR_5$, $NR_6$, $OR_7$ and $COOR_8$, and $R_2$ represents any one selected from the group consisting of H, $NHR_5$, $NR_6$, $OR_7$ and $COOR_8$.

Most particularly, $R_1$ may be $NR_6$ or $OR_7$, and $R_2$ may be H, $OR_7$ or $COOR_8$.

[$X_1$ and $X_2$ in Chemical Formula 1]

Each of $X_1$ and $X_2$ independently represents any one selected from the group consisting of N, S, O and C.

More particularly, each of $X_1$ and $X_2$ may be independently selected from N and C.

[$Y_1$ and $Y_2$ in Chemical Formula 1]

Each of $Y_1$ and $Y_2$ independently represents any one selected from the group consisting of C, S, O and N.

More particularly, each of $Y_1$ and $Y_2$ may be independently selected from S and O.

[$R_3$ in Chemical Formula 1]

$R_3$ represents a substituted or non-substituted heterocyclic group having 1-20 carbon atoms.

Since a heterocycle is a rigid structure, it contributes to improvement of the heat resistance and photo-resistance of the mono-azo dichroic compound represented by Chemical Formula 1.

Particularly, $R_3$ may represent any one selected from the group consisting of: barbituric acid; hydantoin; 3-thiohydantoin; 1,3-indanedione; and dihydrouracil, non-substituted or substituted with at least one selected from the group consisting of alkyl, arylalkyl, aryl, halogen, alkoxy, alkoxyalkyl, alkoxyaryl, nitro, cyano, carboxyl and amide groups. More particularly, $R_3$ may represent any one selected from the group consisting of: barbituric acid; hydantoin; and 3-thiohydantoin, non-substituted or substituted with at least one selected from the group consisting of alkyl, arylalkyl and aryl groups.

Most particularly, the mono-azo dichroic dye compound of Chemical Formula 1 may be any one selected from the compounds represented by the following chemical formulae:

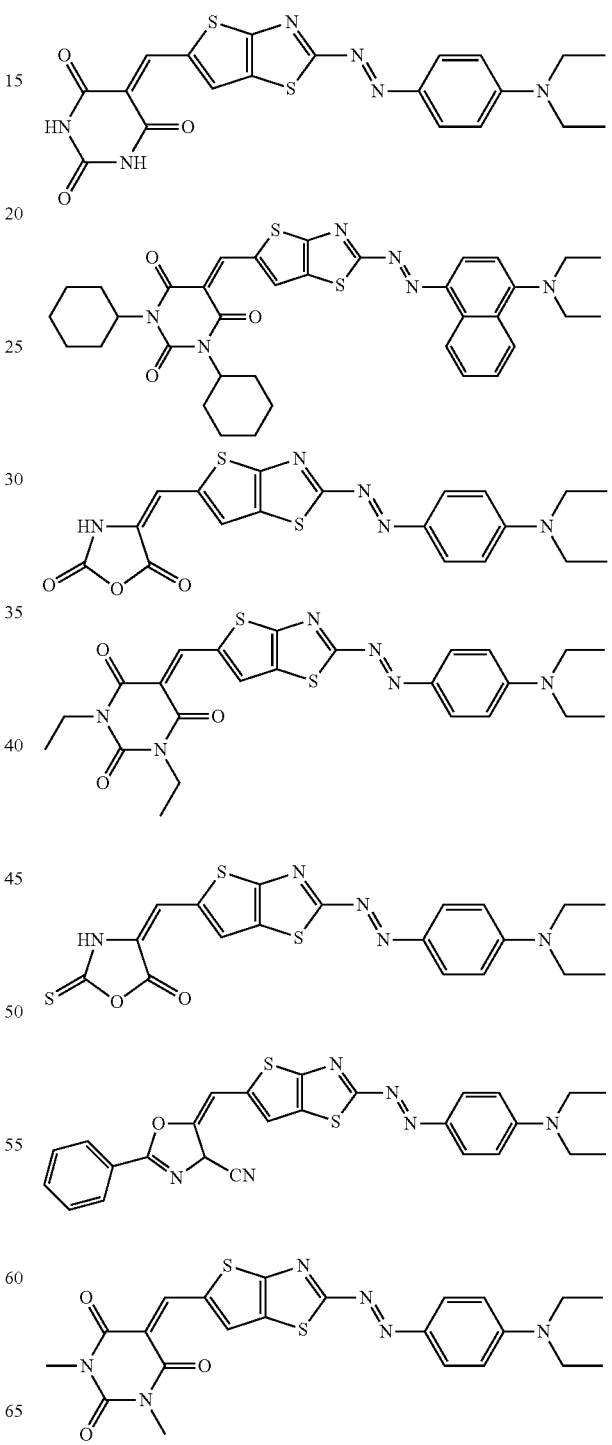

-continued
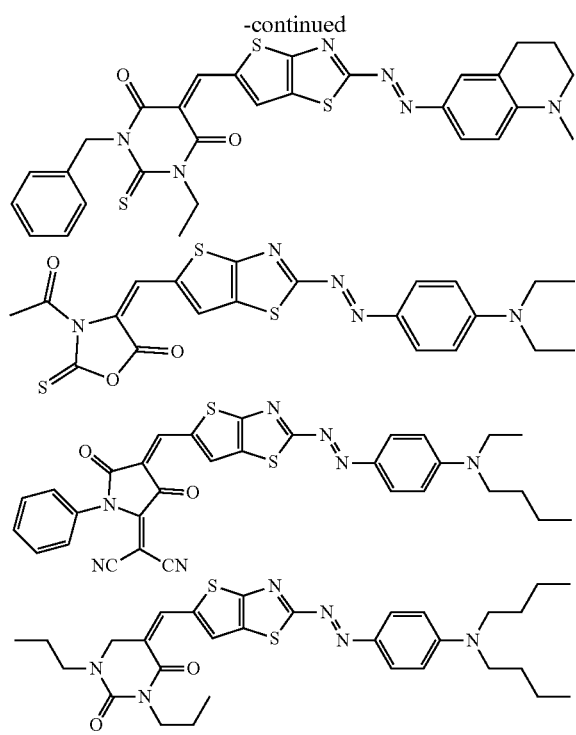
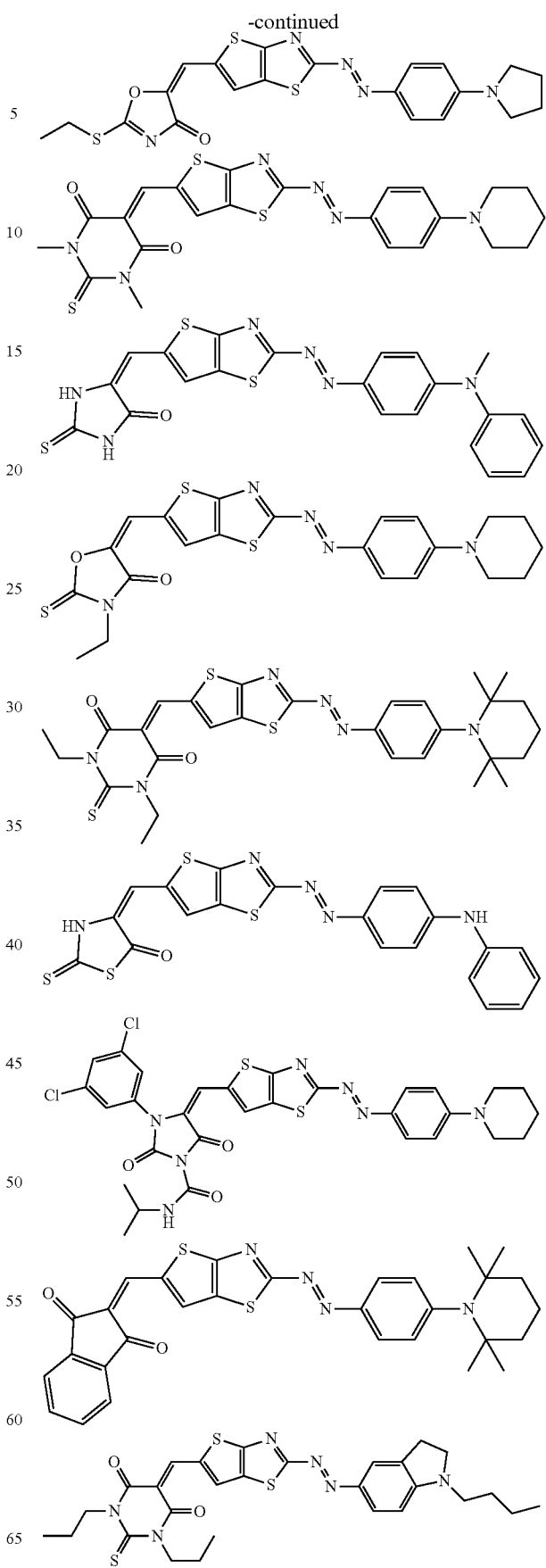

-continued

-continued
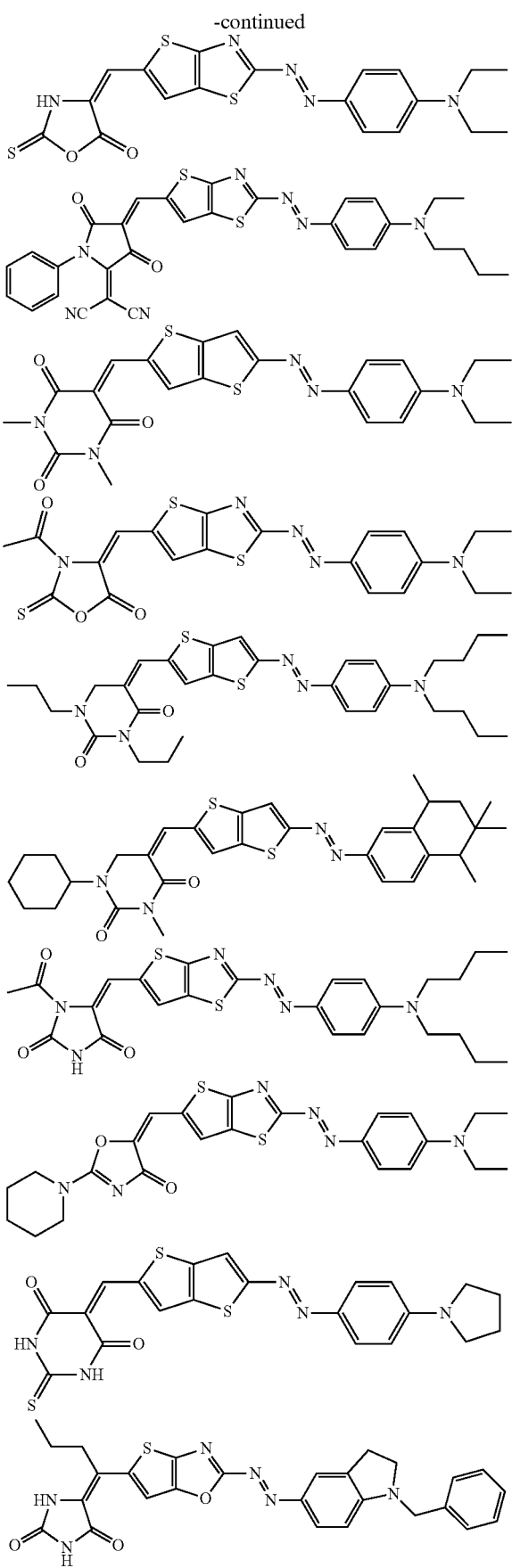
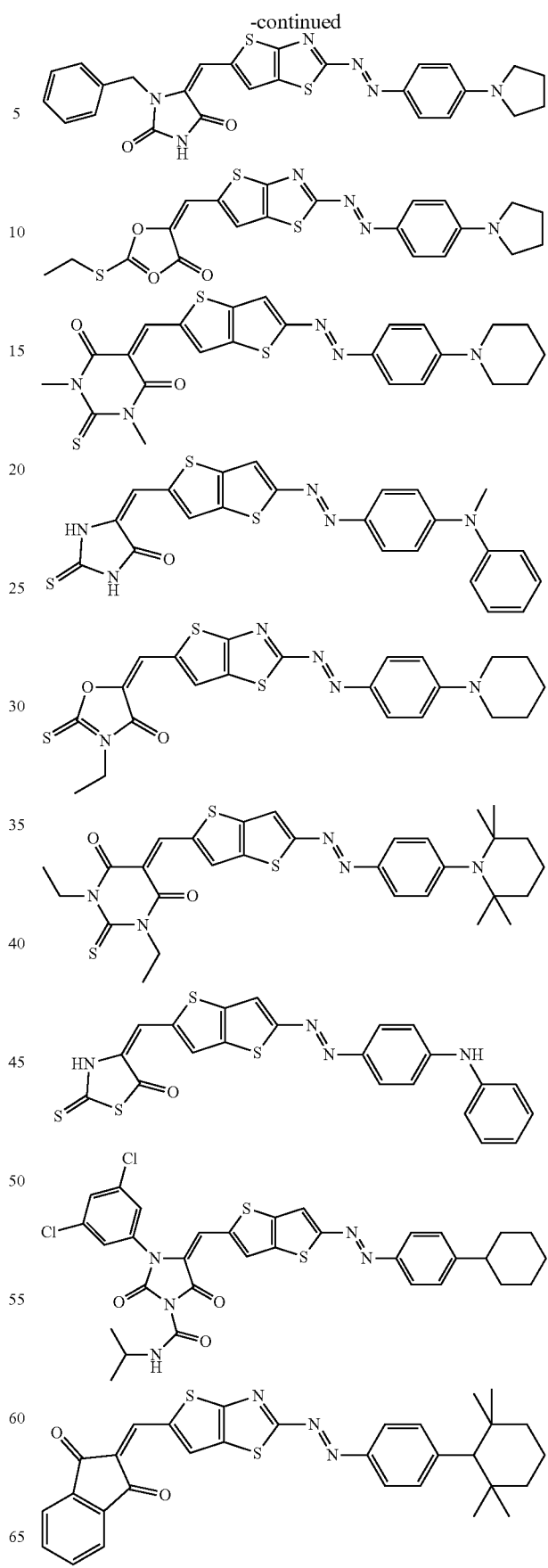

-continued

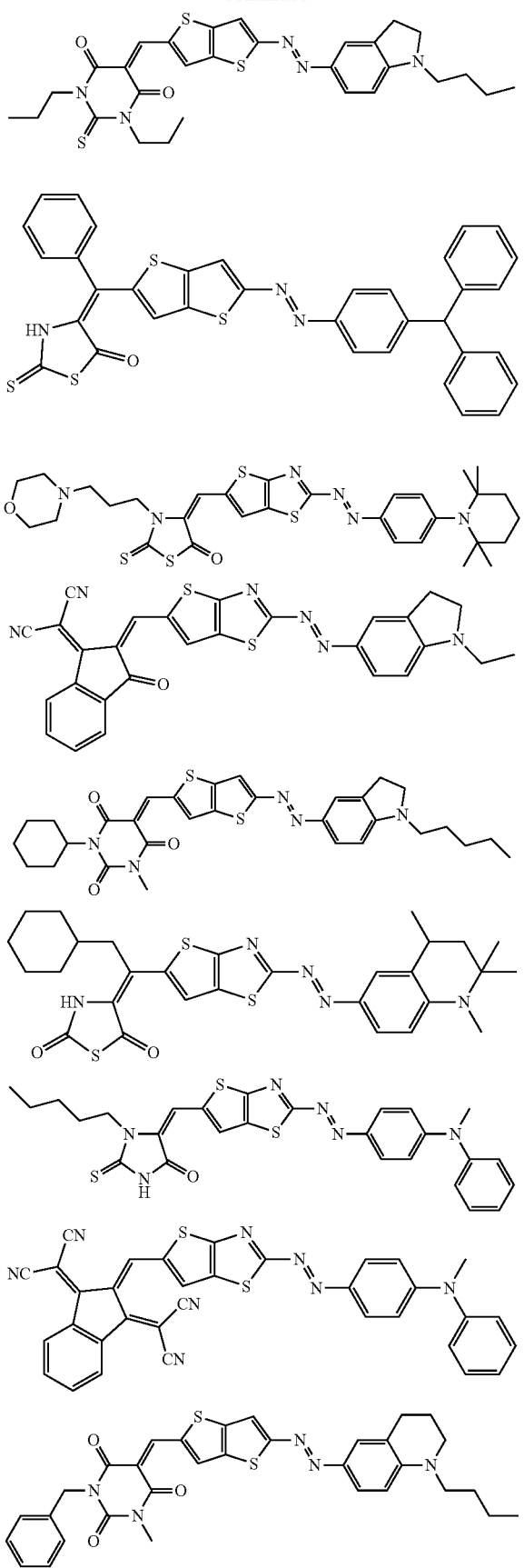

-continued

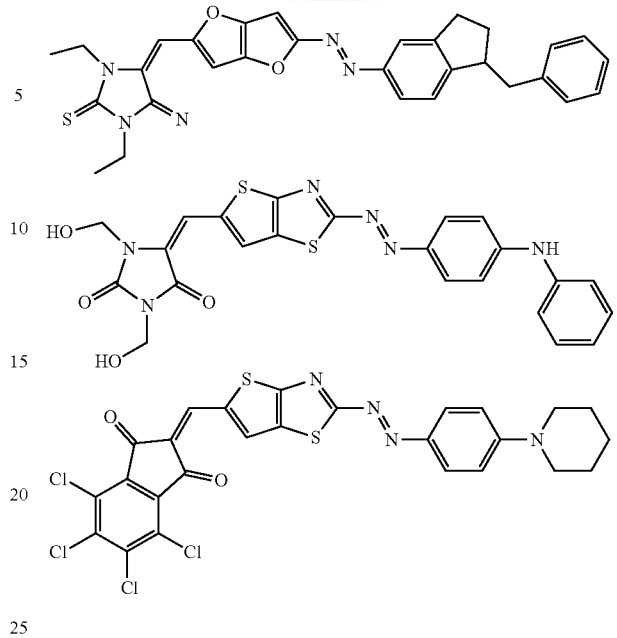

The mono-azo dichroic compound of Chemical Formula 1 may be synthesized through a combination of known organic chemical synthesis processes.

For example, the mono-azo dichroic compound may be synthesized by using a known method with reference to a textbook, such as Dichroic Dyes for Liquid Crystal Display (A. V. lvashchenko, CRC, 1994).

The mono-azo dichroic dye compound according to the present disclosure is combined with a liquid crystal compound to form a composition for a polarizing plate, and the composition is cured to form a polarizing plate. In other words, it is possible to align the mono-azo dichroic dye compound with a high degree of alignment by combining the dichroic dye compound with a liquid crystal compound, while inhibiting deposition of the dichroic dye compound.

Any known low-molecular weight liquid crystal compound and polymeric liquid crystal compound may be used as a liquid crystal compound contained in the composition for a polarizing plate according to the present disclosure. Herein, 'low-molecular weight liquid crystal compound' refers to a liquid crystal compound having no repeating unit in its chemical structure. In addition, 'polymeric liquid crystal compound' refers to a liquid crystal compound having repeating units in its chemical structure. For example, a curable liquid crystal compound may be used in order to improve the alignability of a dichroic dye compound and particular examples of such a liquid crystal compound include 4-(3-acryloyloxypropoxy)benzoic acid o-tolyl ester, or the like.

In the composition for a polarizing plate according to the present disclosure, the mono-azo dichroic dye compound represented by Chemical Formula 1 may be used in an amount of 2-40 wt % based on the total weight of the solid content of the composition, but is not limited thereto.

When preparing the composition for a polarizing plate, a mixture of a dichroic dye showing a red color, a dichroic dye showing a blue color and a dichroic dye showing a green color, or a dichroic dye having a structure realizing dichroism showing a red color, a structure realizing dichroism showing a blue color and a structure realizing dichroism showing a green color may be added, if necessary. The polarizing plate using such a mixture of dichroic dyes may perform linear polarization totally in the visible light region. In addition, in order to carry out color compensation, a dichroic dye showing any color other than red, green and blue, or a dichroic dye including a structure realizing dichroism showing any color other than red, green and blue may be added to the composition for a polarizing plate. When dichroic dyes for a red color, blue color and a green color and a dichroic dye for color compensation are used, they may be combined at any ratio depending on their absorption wavelengths and the ratio is not particularly limited.

Particular examples of other additives include, but are not limited to: a catalyst, a sensitizer, a stabilizer, a chain transfer agent, an inhibitor, an accelerator, a surfactant, a lubricant, a wetting agent, a dispersant, a hydrophobicity-imparting agent, an adhesive, a flow enhancer, an antifoaming agent, a diluent, a colorant, a dye, a pigment, etc. generally known to those skilled in the art. Such ingredients may be selected and combined suitably, as necessary.

In addition, the composition for a polarizing plate may include 1-10 parts by weight, particularly 2-7 parts by weight of a curing agent, if necessary. In other words, when the composition for a polarizing plate is coated on a substrate and a polarizing plate is formed, it is not required to add any separate curing agent to the composition for a polarizing plate in the case of curing using electron beams. However, when the composition for a polarizing plate requires drying in the case of photocuring or thermal curing after the coating, a separate curing agent is added to the composition for a polarizing plate.

Any curing agent used conventionally in the art may be used. Particular examples of a photopolymerization initiator using ultraviolet rays include at least one selected from the group consisting of at least one active halogen compound selected from halomethyloxadiazole compounds and halomethyl-s-triazine compounds, 3-aryl substituted coumarin compounds, benzophenone compounds, acetophenone compounds and derivatives thereof, cyclopentadiene-benzene-iron complexes and salts thereof, and oxime compounds. Particular examples of the active halogen compound, which is a halomethyloxadiazole compound, include 2-halomethyl-5-vinyl-1,3,4-oxadiazole compounds, 2-trichloromethyl-5-styryl-1,3,4-oxadiazole, 2-trichloromethyl-5-(p-cyanostyryl)-1,3,4-oxadiazole, 2-trichloromethyl-5-(p-methoxystyryl)-2,3,4-oxadiazole, or the like. Particular examples of the active halogen compound, which is a halomethyl-s-triazine compound, include vinyl-halomethyl-s-triazine compounds, 2-(naphtho-1-yl)-4,6-bis-halomethyl-s-triazine compound and 4-(p-aminophenyl)-2,6-di-halomethyl-s-triazine compound, or the like.

Particular examples of the photoinitiator include Irgacure series (e.g. Irgacure 651, Irgacure 184, Irgacure 500, Irgacure 1000, Irgacure 149, Irgacure 819, Irgacure 261) and Darocure series (e.g. Darocure 1173) available from Ciba Specialty Chemicals, 4,4'-bis(diethylamino)-benzophenone, 2-(O-benzoyloxime)-1-[4-(phenylthiol)phenyl]-1,2-octanedione, 1-(O-acetyloxime)-1-[9-ethyl-6-(2-methylbenzoyl)-9H-carbazol-3-yl]ethanone, 2-benzyl-2-dimethylamino-4-morpholinobutyrophenone, 2,2-dimethoxy-2-phenylacetophenone, 2-(o-chlorophenyl)-4,5-diphenylimidazolyl dimer, 2-(o-fluorophenyl)-4,5-diphenylimidazolyl dimer, 2-(o-methoxyphenyl)-4,5-diphenylimidazolyl dimer, 2-(p-methoxyphenyl)-4,5-diphenylimidazolyl dimer, 2-(p-dimethoxyphenyl)-4,5-diphenylimidazolyl dimer, 2-(2,4-dimethoxyphenyl)-4,5-diphenylimidazolyl dimer, 2-(p-mercaptophenyl)-4,5-diphenylimidazolyl dimer, benzoin isopropyl ether, or the like. Such curing agents may be used alone or in combination.

To carry out coating with the composition for a polarizing plate, a suitable solvent may be selected and used for combining the ingredients, including the mono-azo dichroic dye compound, with one another. The solvent and solid content in the composition are not particularly limited, but may be selected and used by those skilled in the art to meet the objects of the present disclosure.

The substrate coated with the composition for a polarizing plate to form a polarizing plate may be a glass plate or plastic substrate. Particular examples of the plastic substrate include but are not limited to those made of acrylic resin, polycarbonate resin, epoxy resin or polyester resin.

The composition for a polarizing plate may be applied to the substrate through a thin film coating process used currently in the art, such as spin coating, blade coating, casting coating or roll coating. The composition for a polarizing plate may be coated so that the finally cured polarizing plate may have a thickness of 0.1-10 micrometers, particularly 0.3-7 micrometers, but is not limited thereto. When curing the composition for a polarizing plate after the coating, a known curing process, such as electron beam curing, thermal curing or UV curing, may be used, but the curing process is not particularly limited.

Meanwhile, when the polarizing plate obtained by using a dichroic dye is used for a liquid crystal display (LCD), the alignability of the coated dichroic dye is regarded as important. Therefore, the substrate itself may be provided with alignability or a separate aligning film may be formed to impart alignability to the substrate in order to improve the alignability of the dichroic dye, before coating the polarizing plate using the composition for a polarizing plate.

The alignability to the substrate may be obtained by forming surface irregularities on the surface of the substrate to impart orientability to the molecules forming the coating film. In addition, a method for imparting alignability to the substrate may be used, the method including: forming a separate aligning film formed of an azo-based compound, polyimide, polyamide, cinnamate or amic acid on the substrate, and subjecting the aligning film to a rubbing or photo-alignment process to impart alignability. As a non-contact surface treatment method, a photo-alignment method may also be used, the method including irradiating polarized UV rays to the polarizing plate to impart anisotropic property to the coating film.

If necessary, the surface of the polarizing plate formed by using the mono-azo dichroic dye compound according to the present disclosure may be subjected to post-treatment through antistatic treatment, corona treatment, hard coating treatment, antireflection treatment, antiglare treatment, or the like.

The polarizing plate obtained by the above-described method has a high dichroic ratio, shows excellent durability, such as heat resistance and photo-resistance, under a high-temperature and high-humidity condition, and causes little discoloration or degradation of polarizability, and thus may be used for optical devices, such as car dash boards, airplanes and liquid crystal projectors, requiring high heat resistance, durability and polarizability. The polarizing plate may have a dichroic ratio (D0) of 19-25, heat resistance ($\Delta$ intensity) of 6% or less, and a photo-resistance ($\Delta$ intensity) of 3% or less. Herein, each of the dichroic ratio (D0), a heat resistance ($\Delta$ intensity) and the photo-resistance ($\Delta$ intensity) of the polarizing plate means the value determined by each of the evaluation methods as defined in the following parts of 'Evaluation of Dichroic Ratio', 'Evaluation of Heat Resistance' and 'Evaluation of Photo-resistance'.

Hereinafter, the present disclosure will be explained in more detail with reference to exemplary embodiments. This disclosure may, however, be embodied in many different forms and should not be construed as limited to the exemplary embodiments set forth therein. It will be apparent that these exemplary embodiments are provided so that the present disclosure will be complete and understood easily by those skilled in the art.

<Determination of Compound Structure>

The structure of a compound was determined by using a LC mass spectrometer. A compound to be determined was dissolved in THF and used for determination. The peaks were analyzed to determine the m/z value.

<Evaluation of Photo-Resistance>

Photo-resistance was evaluated by exposing each of the polarizing plates according to Examples and Comparative Examples to Redlenser Flash LED LENSER P7R(9408R) at 1000 lm for 1 hour and measuring absorbance. Herein, photo-resistance was evaluated from a difference between the initial absorbance and the absorbance after exposure.

Photo-resistance (Δ Intensity)=[(Absorbance after exposure at 1000 lm for 1 hour)−(Initial absorbance)]×100 (%)

<Evaluation of Heat Resistance>

Heat resistance was evaluated from a difference between the initial absorbance and the absorbance determined after allowing each of the polarizing plates according to Examples and Comparative Examples to stand in a constant-temperature and constant-humidity system at 80° C. for 250 hours.

Heat resistance (Δ Intensity)=[(Absorbance after 250 hours)−(Initial absorbance)]×100 (%)

<Evaluation of Dichroic Ratio>

The dichroic ratio was calculated according to the following formula, after measuring the absorbance of each of the polarizing plates according to Examples and Comparative Examples in a wavelength range of 550-700 nm by using a multichannel spectrometer, while a linear polarizer was inserted to the light source side of an optical microscope.

Dichroic ratio (D0)=$Az0/Ay0$ wherein Az0 represents the absorbance to the polarized light in the direction of absorption axis of a light-absorbing polarizing plate, and Zy0 represents the absorbance in the direction of polarization axis of the polarizing plate.

Synthesis Examples

Synthesis of Intermediate 1-1

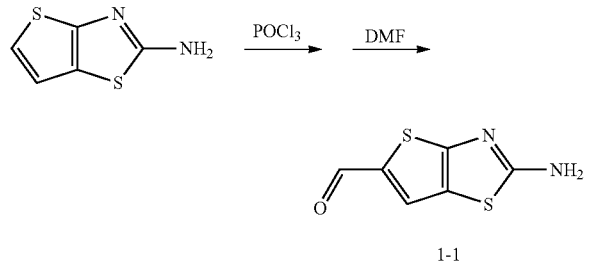

First, phosphoryl trichloride (1.27 g, 8.3 mmol) was added dropwise gradually to 10 mL of dimethyl formamide (DMF) at 0° C. under nitrogen atmosphere, and the resultant mixture was agitated for 1 hour. Next, thieno[2,3-d]thiazol-2-amine (1 g, 6.4 mmol) was introduced thereto and the resultant mixture was warmed to 80° C. and agitated to carry out reaction. Then, the resultant mixture was cooled to room temperature and 30 mL of water was added thereto to quench the reaction. After introducing 30 mL of 1 N NaOH to the resultant solid, 50 mL of chloroform was further introduced and dissolved. Then, the resultant product was washed twice with water, the organic layer was separated, dry magnesium sulfate was added thereto, the resultant product was agitated and filtered, and the filtrate was distilled under reduced pressure. The concentrated compound was purified through a silica column by using chloroform and ethyl acetate to obtain solid intermediate 1-1 (0.91 g, 77%, MS: [M+H]$^+$=184.0).

Synthesis of Intermediate 1-2

Intermediate 1-1 (1 g, 5.4 mmol) was introduced to 3 mL of acetic acid and 7 mL of propionic acid at 0° C., and the resultant mixture was agitated for 30 minutes. Next, sodium nitrite (0.39 g, 5.7 mmol) was dissolved in 16 mL of sulfuric acid and added dropwise gradually thereto, and the resultant mixture was agitated for 30 minutes, while maintaining the temperature at 5° C. or lower. N,N-diethylaniline (1.2 g, 8.1 mmol) was dissolved in 5 mL of methanol and added dropwise gradually thereto, and the resultant mixture was agitated for 2 hours. Herein, the reaction mixture was titrated with 2 N aqueous sodium acetate solution to maintain pH 5-7. After completing the reaction, the mixture was filtered and washed twice with water and methanol to obtain solid intermediate 1-2 (1.4 g, 75%, MS: [M+H]$^+$=345.1).

Synthesis Example 1

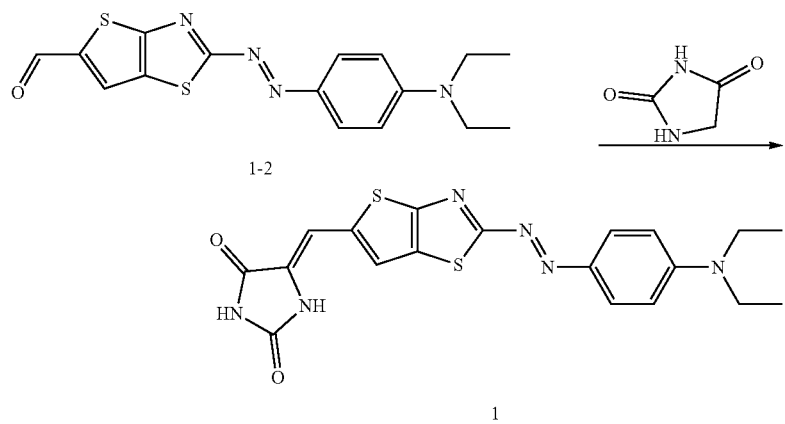

Intermediate 1-2 (0.5 g, 1.5 mmol) and imidazoline-2,4-dione (0.16 g, 1.6 mmol) were added to 20 mL of acetic acid. Next, ammonium acetate (0.2 g, 2.76 mmol) was added thereto and the resultant mixture was refluxed for 6 hours. The reaction mixture was cooled to room temperature and the reaction was quenched with sodium bicarbonate. The resultant product was extracted with 20 mL of chloroform and 20 mL of water three times. Then, the resultant product was dried with magnesium sulfate, the solvent was evaporated, and the product was purified through a silica column by using chloroform and ethyl acetate to obtain Compound 1 (0.31 g, 50%, MS: [M+H]$^+$=426.1).

Synthesis Example 2

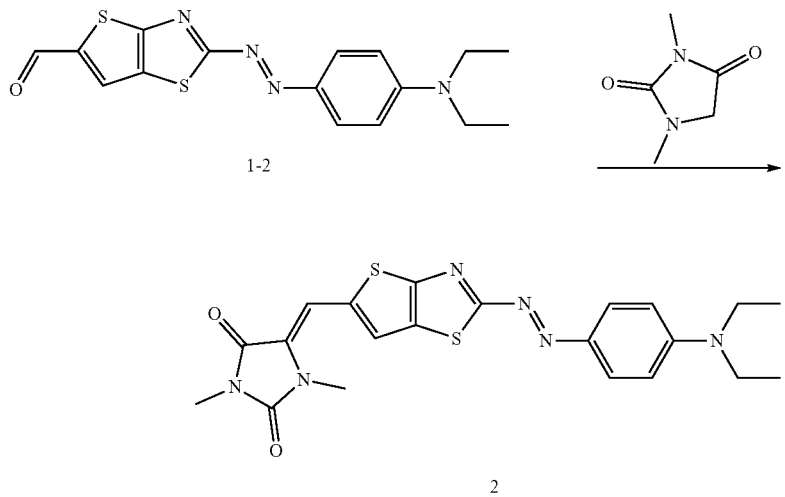

Compound 2 (0.27 g, 41%, MS: [M+H]$^+$=454.1) was obtained in the same manner as Synthesis Example 1, except that 1,3-dimethylimidazoline-2,4-dione was used instead of imidazoline-2,4-dione.

Synthesis Example 3

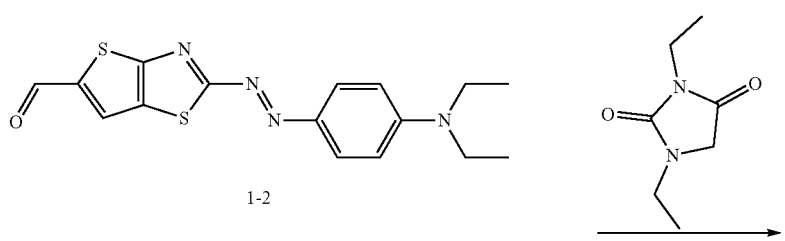

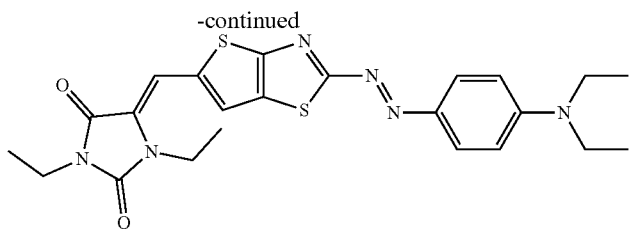

3

Compound 3 (0.34 g, 49%, MS: [M+H]⁺=482.2) was obtained in the same manner as Synthesis Example 1, except that 1,3-diethylimidazoline-2,4-dione was used instead of imidazoline-2,4-dione.

Synthesis Example 4

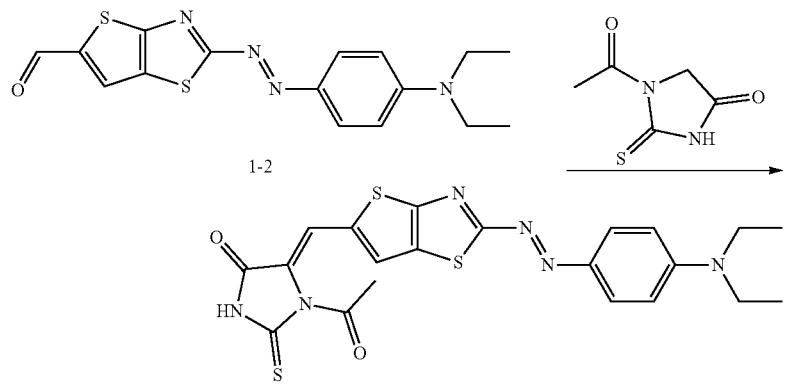

4

Compound 4 (0.33 g, 47%, MS: [M+H]⁺=487.1) was obtained in the same manner as Synthesis Example 1, except that 1-acetyl-2-thioxo-imidazoline-4-one was used instead of imidazoline-2,4-dione.

Synthesis Example 5

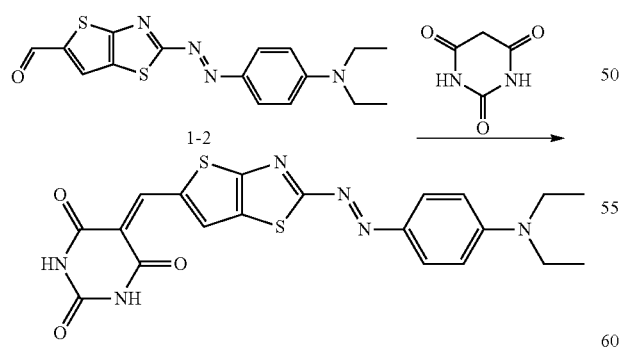

5

Compound 5 (0.29 g, 44%, MS: [M+H]⁺=454.1) was obtained in the same manner as Synthesis Example 1, except that barbituric acid was used instead of imidazoline-2,4-dione.

Synthesis Example 6

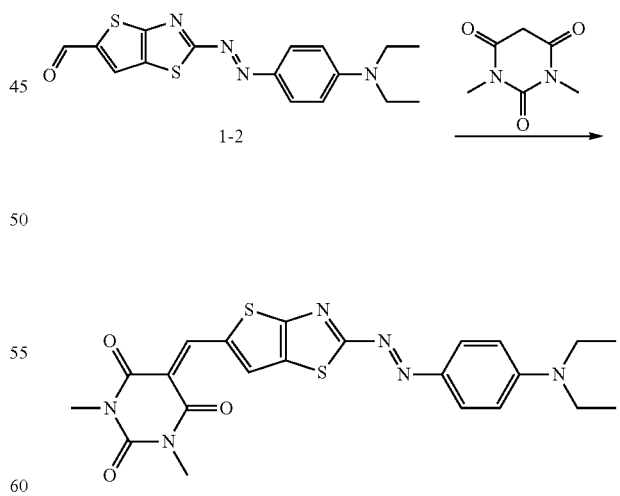

6

Compound 6 (0.37 g, 53%, MS: [M+H]⁺=483.1) was obtained in the same manner as Synthesis Example 1, except that 1,3-dimethylbarbituric acid was used instead of imidazoline-2,4-dione.

Synthesis Example 7

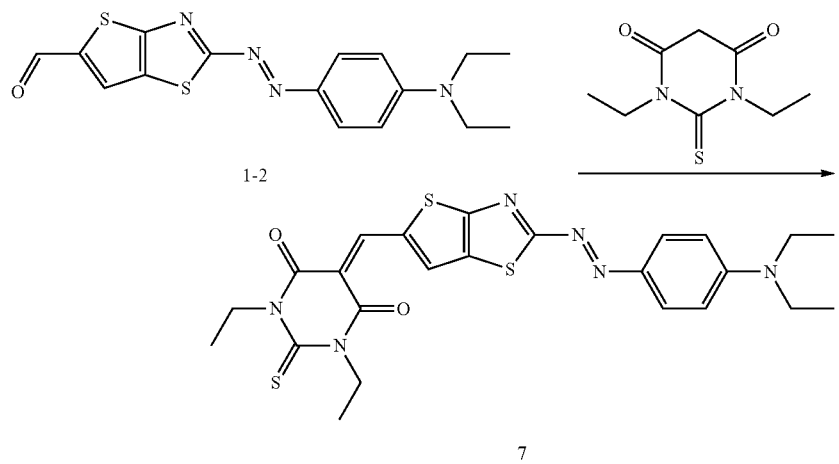

Compound 7 (0.34 g, 45%, MS: [M+H]$^+$=526.1) was obtained in the same manner as Synthesis Example 1, except that 1,3-diethyl-2-thiobarbituric acid was used instead of imidazoline-2,4-dione.

Synthesis Example 8

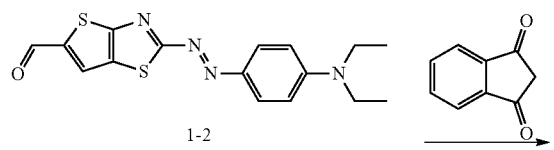

-continued

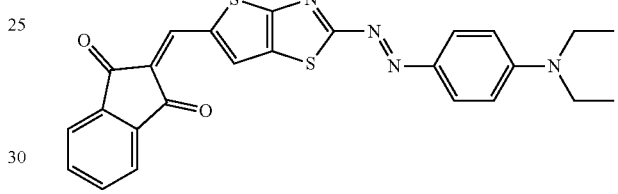

Compound 8 (0.31 g, 45%, MS: [M+H]$^+$=472.1) was obtained in the same manner as Synthesis Example 1, except that 1,3-indanedione was used instead of imidazoline-2,4-dione.

Synthesis Example 9

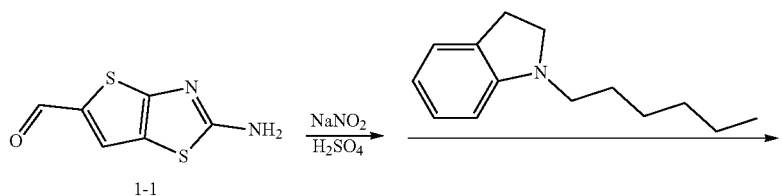

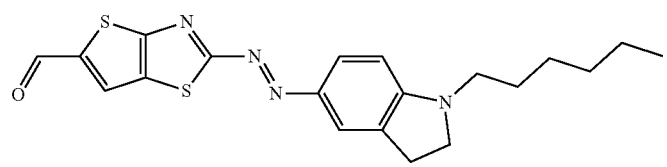

Intermediate 9-1 (1.5 g, 69%, MS: [M+H]$^+$=399.0) was obtained in the same manner as Synthesis of Intermediate 1-2, except that 1-hexylindoline was used instead of N,N-diethylaniline.

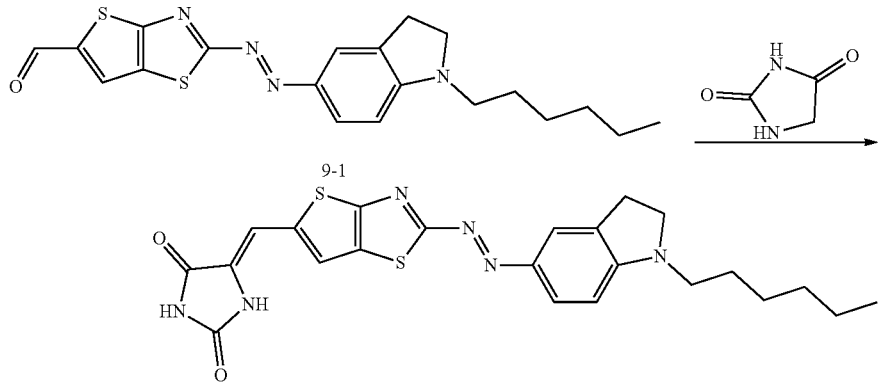

Compound 9 (0.28 g, 46%, MS: [M+H]$^+$=480.1) was obtained in the same manner as Synthesis Example 1, except that Intermediate 9-1 was used instead of Intermediate 1-2.

Synthesis Example 10

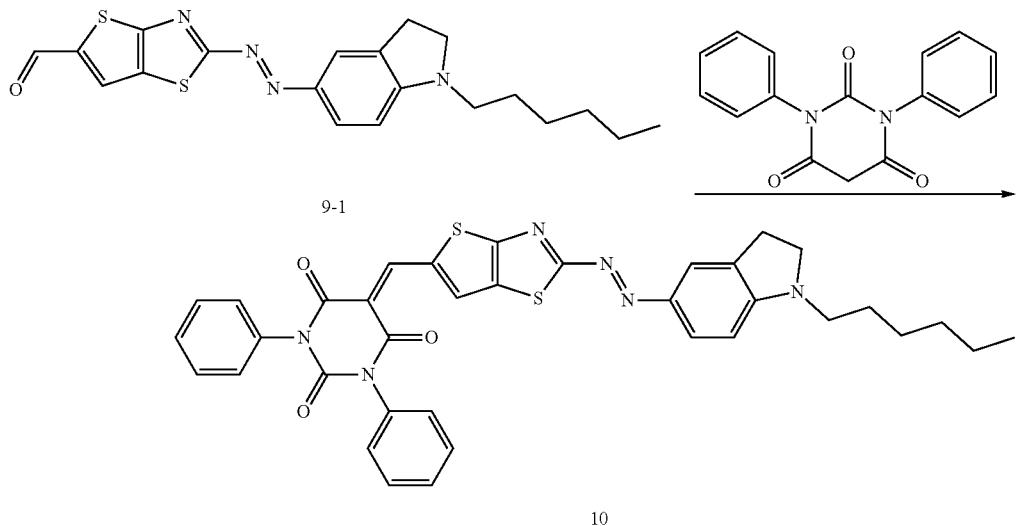

Compound 10 (0.55 g, 66%, MS: [M+H]$^+$=660.2) was obtained in the same manner as Synthesis Example 9, except that 1,3-diphenylbarbituric acid was used instead of imidazoline-2,4-dione.

Synthesis Example 11

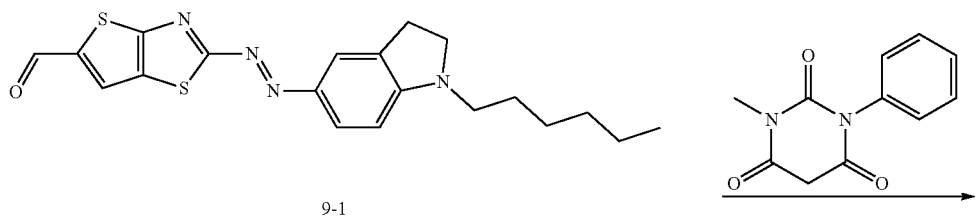

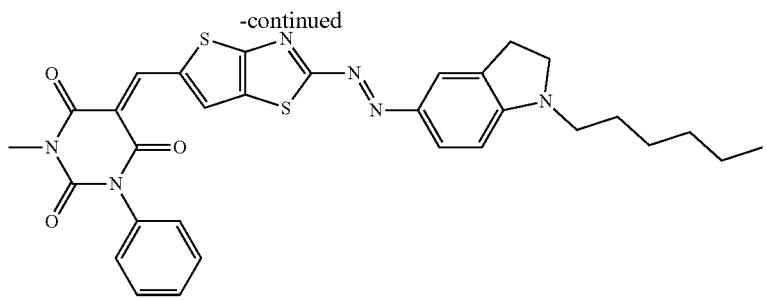

11

Compound 11 (0.42 g, 56%, MS: [M+H]$^+$=598.2) was obtained in the same manner as Synthesis Example 9, except that 1-methyl-3-phenylbarbituric acid was used instead of imidazoline-2,4-dione.

Synthesis Example 12

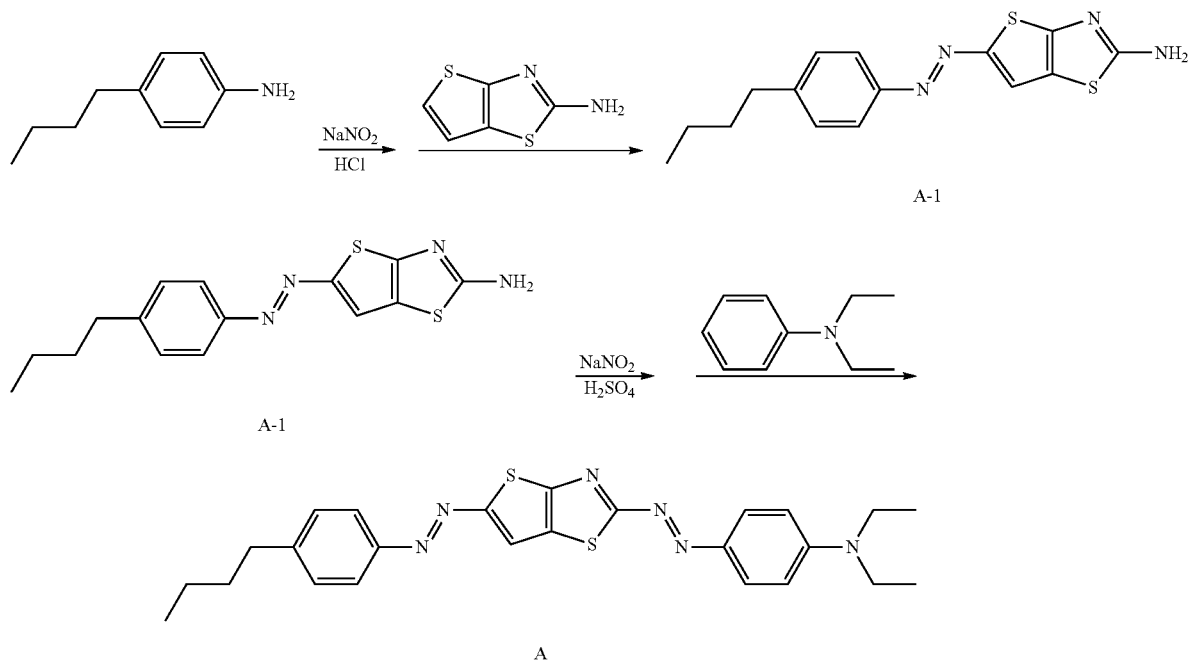

First, 4-butylaniline (2 g, 13.4 mmol) was added to 10 mL of hydrochloric acid, 5 mL of aqueous sodium nitrite solution (1.017 g, 14.7 mmol) was added dropwise thereto, and the resultant mixture was agitated for 30 minutes. Next, 0.08 g of sulfamic acid was added thereto and the resultant mixture was further agitated for 30 minutes. Thieno[2,3-d]thiazol-2-amine (0.3 g, 6.7 mmol) was dissolved in 10 mL of methanol and the resultant solution was added dropwise gradually, and then the resultant mixture was agitated for 2 hours. After completing the reaction, the resultant product was washed with 30 mL of methanol and 30 mL of water and filtered to obtain Intermediate A-1. Then, solid Compound A (0.28 g, 37%, MS: [M+H]$^+$=476.2) was obtained in the same manner as Synthesis of Intermediate 1-2, except that Intermediate A-1 was used instead of Intermediate 1-1.

Synthesis Example 13

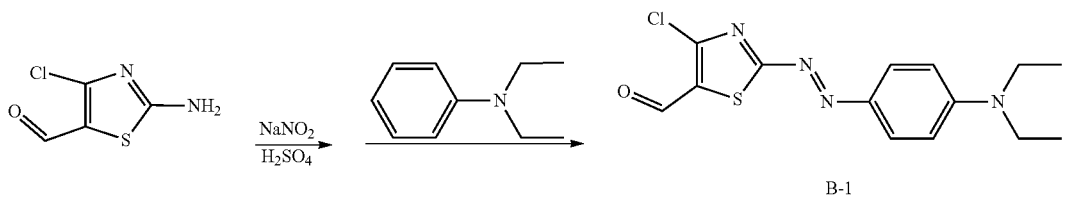

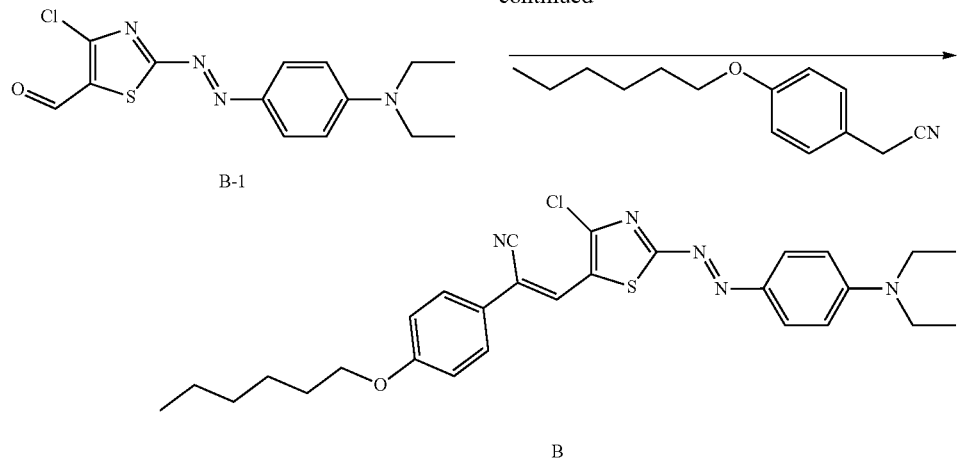

First, 2-amino-4-chlorothiazol-5-carboaldehyde (2 g, 12.3 mmol) was added to 10 mL of sulfuric acid and 5 mL of aqueous sulfuric acid solution of sodium nitrite (1.018 g, 14.8 mmol) was added dropwise thereto, and the resultant mixture was agitated for 30 minutes. Next, 0.08 g of sulfamic acid was further introduced thereto and the resultant mixture was further agitated for 30 minutes. Then, N,N-diethylaniline (1.1 g, 7.4 mmol) was dissolved in 10 mL of methanol and the resultant solution was added dropwise gradually, and the resultant mixture was agitated for 2 hours. After completing the reaction, the resultant product was washed with 30 mL of methanol and 30 mL of water and filtered to obtain Intermediate B-1. Then, solid Compound B (1.33 g, 83%, MS: [M+H]$^+$=521.2) was obtained in the same manner as Synthesis Example 2, except that Intermediate B-1 was used instead of Intermediate 1-2.

<Manufacture of Polarizing Plate>

Preparation Example 1

First, 2 wt % of an aligning layer-forming solution (prepared by dissolving 2 wt % of polyacrylate having methoxy cinnamate (MPN-Ci) as a photosensitive functional group in the form of a branch in 98% of cyclopentanone (CPO)) was spin-coated on a cycloolefin polymer (COP) film at 1000 rpm for 10 seconds, dried at 80° C. for 2 minutes, and cured with UVB at a dose of 250 mJ. A composition including the dichroic dye of Synthesis Example 1 according to the ingredients at the mixing ratio as shown in the following Table 1 was dissolved in cyclopentanone at room temperature to obtain a solution of composition for a polarizing plate having a solid content of 26 wt %. Since the composition included 5 wt % of a curing agent in the reactive liquid crystal itself, any separate curing agent was not added to the composition.

TABLE 1

| Composition for Polarizing Plate | | Content (parts by weight) |
|---|---|---|
| Curable liquid crystal | RSD-1 (Sundia Co., China) | 75 |
| | RSM-1 (LG Chem.) | 25 |
| Dichroic dye | Synthesis Example 1 | 2.0 |
| PI | Irgacure 369 (Ciba Specialty Chemicals) | 2.0 |

TABLE 1-continued

| Composition for Polarizing Plate | | Content (parts by weight) |
|---|---|---|
| Surf. | BYK-358N (BYK Co.) | 1.0 |
| Solvent | Cyclopentanone | |

The composition for a polarizing plate was spin coated on the top of a photoalignment-treated aligning layer at 1000 rpm for 30 seconds. Then, the spin coated polarizing film-forming composition was dried at 120° C. for 2 minutes. To carry out photo-crosslinking of the liquid crystal and dye ingredients, the coating layer was cured with a UVB lamp at 250 mJ under N$_2$ gas atmosphere. The cured polarizing plate film had a thickness of 0.9 μm.

Preparation Example 2

A polarizing plate film was obtained in the same manner as Preparation Example 1, except that Compound 2 according to Synthesis Example 2 was used instead of Compound 1 according to Synthesis Example 1.

Preparation Example 3

A polarizing plate film was obtained in the same manner as Preparation Example 1, except that Compound 3 according to Synthesis Example 3 was used instead of Compound 1 according to Synthesis Example 1.

Preparation Example 4

A polarizing plate film was obtained in the same manner as Preparation Example 1, except that Compound 4 according to Synthesis Example 4 was used instead of Compound 1 according to Synthesis Example 1.

Preparation Example 5

A polarizing plate film was obtained in the same manner as Preparation Example 1, except that Compound 5 according to Synthesis Example 5 was used instead of Compound 1 according to Synthesis Example 1.

Preparation Example 6

A polarizing plate film was obtained in the same manner as Preparation Example 1, except that Compound 6 according to Synthesis Example 6 was used instead of Compound 1 according to Synthesis Example 1.

Preparation Example 7

A polarizing plate film was obtained in the same manner as Preparation Example 1, except that Compound 7 according to Synthesis Example 7 was used instead of Compound 1 according to Synthesis Example 1.

Preparation Example 8

A polarizing plate film was obtained in the same manner as Preparation Example 1, except that Compound 8 according to Synthesis Example 8 was used instead of Compound 1 according to Synthesis Example 1.

Preparation Example 9

A polarizing plate film was obtained in the same manner as Preparation Example 1, except that Compound 9 according to Synthesis Example 9 was used instead of Compound 1 according to Synthesis Example 1.

Preparation Example 10

A polarizing plate film was obtained in the same manner as Preparation Example 1, except that Compound 10 according to Synthesis Example 10 was used instead of Compound 1 according to Synthesis Example 1.

Preparation Example 11

A polarizing plate film was obtained in the same manner as Preparation Example 1, except that Compound 11 according to Synthesis Example 11 was used instead of Compound 1 according to Synthesis Example 1.

Comparative Example 1

A polarizing plate film was obtained in the same manner as Preparation Example 1, except that Compound A according to Synthesis Example 12 was used instead of Compound 1 according to Synthesis Example 1.

Comparative Example 2

A polarizing plate film was obtained in the same manner as Preparation Example 1, except that Compound B according to Synthesis Example 13 was used instead of Compound 1 according to Synthesis Example 1.

Each of the polarizing plates were evaluated in terms of its dichroic ratio, heat resistance and photo-resistance. The results are shown in the following Table 2.

TABLE 2

|  | Dichroic ratio | Heat resistance | Photo-resistance |
|---|---|---|---|
| Prep. Ex. 1 | 21.10 | 4.6% | 2.2% |
| Prep. Ex. 2 | 23.08 | 2.9% | 1.9% |
| Prep. Ex. 3 | 22.12 | 3.1% | 2.7% |
| Prep. Ex. 4 | 19.89 | 5% | 2.4% |
| Prep. Ex. 5 | 24.50 | 2.8% | 1.9% |
| Prep. Ex. 6 | 19.99 | 4.8% | 2.6% |
| Prep. Ex. 7 | 20.09 | 4.8% | 2.7% |
| Prep. Ex. 8 | 22.18 | 3.1% | 2.1% |
| Prep. Ex. 9 | 23.44 | 2.7% | 2.8% |
| Prep. Ex. 10 | 20.19 | 3.8% | 2.7% |

TABLE 2-continued

|  | Dichroic ratio | Heat resistance | Photo-resistance |
|---|---|---|---|
| Prep. Ex. 11 | 20.11 | 3.6% | 2.8% |
| Comp. Ex. 1 | 19.73 | 5% | 3% |
| Comp. Ex. 2 | 5.3 | 29.8% | 24.1% |

It can be seen from Table 2 that the polarizing plates according to Preparation Examples of the present disclosure has an improved dichroic ratio and excellent photo-resistance and heat resistance, as compared to Comparative Examples.

What is claimed is:

1. A mono-azo dichroic dye compound represented by Chemical Formula 1:

[Chemical Formula 1]

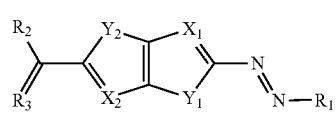

wherein $R_1$ is selected from the group consisting of: substituted or non-substituted aryl groups having 6-20 carbon atoms, substituted or non-substituted heteroaryl groups having 3-20 carbon atoms, substituted or non-substituted alkyl groups having 1-20 carbon atoms, $-NR_4OH$, $-NHR_5$, $-NR_6$, $-OR_7$, $-COOR_8$, $-OCOR_9$, $-SR_{10}$, halogen groups, $-OH$, $-CN$, $-COOH$, $-PO_3$, $-SO_3$, and $-NO_2$;

wherein $R_2$ is selected from the group consisting of: H, substituted or non-substituted aryl groups having 6-20 carbon atoms, substituted or non-substituted heteroaryl groups having 3-20 carbon atoms, substituted or non-substituted alkyl groups having 1-20 carbon atoms, $-NR_4OH$, $-NHR_5$, $-NR_6$, $-OR_7$, $-COOR_8$, $-OCOR_9$, $-SR_{10}$, halogen groups, $-OH$, $-CN$, $-COOH$, $-PO_3$, $-SO_3$, and $-NO_2$;

$R_3$ is a substituted or non-substituted heterocyclic group having 2-20 carbon atoms, or 1,3-indanedione non-substituted or substituted with one or more of alkyl, arylalkyl, aryl, halogen, alkoxy, alkoxyalkyl, alkoxyaryl, nitro, cyano, carboxyl and amide groups;

wherein each of $R_4$-$R_{10}$ is independently H or a group having 1-20 carbon atoms selected from the group consisting of: alkoxy groups, or alkoxyalkyl groups; halogen-containing alkyl groups; heterocyclic groups, aryl groups, non-substituted or substituted with one or more of alkoxy groups, alkoxyalkyl groups, halogens and alkyl groups;

each of $X_1$ and $X_2$ is independently selected from the group consisting of N, S, O and C; and each of $Y_1$ and $Y_2$ selected from the group consisting of C, S, O and N.

2. The mono-azo dichroic dye compound according to claim 1, wherein $R_1$ is selected from the group consisting of $-CN$, $-OH$, $-NHR_5$, $-NR_6$, $-OR_7$ and $-COOR_8$, and $R_2$ is selected from the group consisting of H, $-CN$, $-OH$, $-NHR_5$, $-NR_6$, $-OR_7$ and $-COOR_8$.

3. The mono-azo dichroic dye compound according to claim 1, wherein $R_1$ is selected from the group consisting of $-NHR_5$, $-NR_6$, $-OR_7$ and $-COOR_8$, and $R_2$ is selected from the group consisting of H, $-NHR_5$, $-NR_6$, $-OR_7$ and $-COOR_8$.

4. The mono-azo dichroic dye compound according to claim 1, wherein $R_1$ is —$NR_6$ or —$OR_7$, and $R_2$ is H, —$OR_7$ or —$COOR_8$.

5. The mono-azo dichroic dye compound according to claim 1, wherein each of $X_1$ and $X_2$ is independently selected from N and C.

6. The mono-azo dichroic dye compound according to claim 1, wherein each of $Y_1$ and $Y_2$ is independently selected from S and O.

7. The mono-azo dichroic dye compound according to claim 1, wherein $R_3$ is selected from the group consisting of: barbituric acid, hydantoin, 3-thiohydantoin, 1,3-indanedione, and dihydrouracil, non-substituted or substituted with at least one selected from the group consisting of alkyl, arylalkyl, aryl, halogen, alkoxy, alkoxyalkyl, alkoxyaryl, nitro, cyano, carboxyl and amide groups.

8. The mono-azo dichroic dye compound according to claim 1, wherein $R_3$ is selected from the group consisting of: barbituric acid, hydantoin, and 3-thiohydantoin, non-substituted or substituted with at least one selected from the group consisting of alkyl, arylalkyl and aryl groups.

9. The mono-azo dichroic dye compound according to claim 1, which is any one selected from the compounds represented by the following chemical formulae:

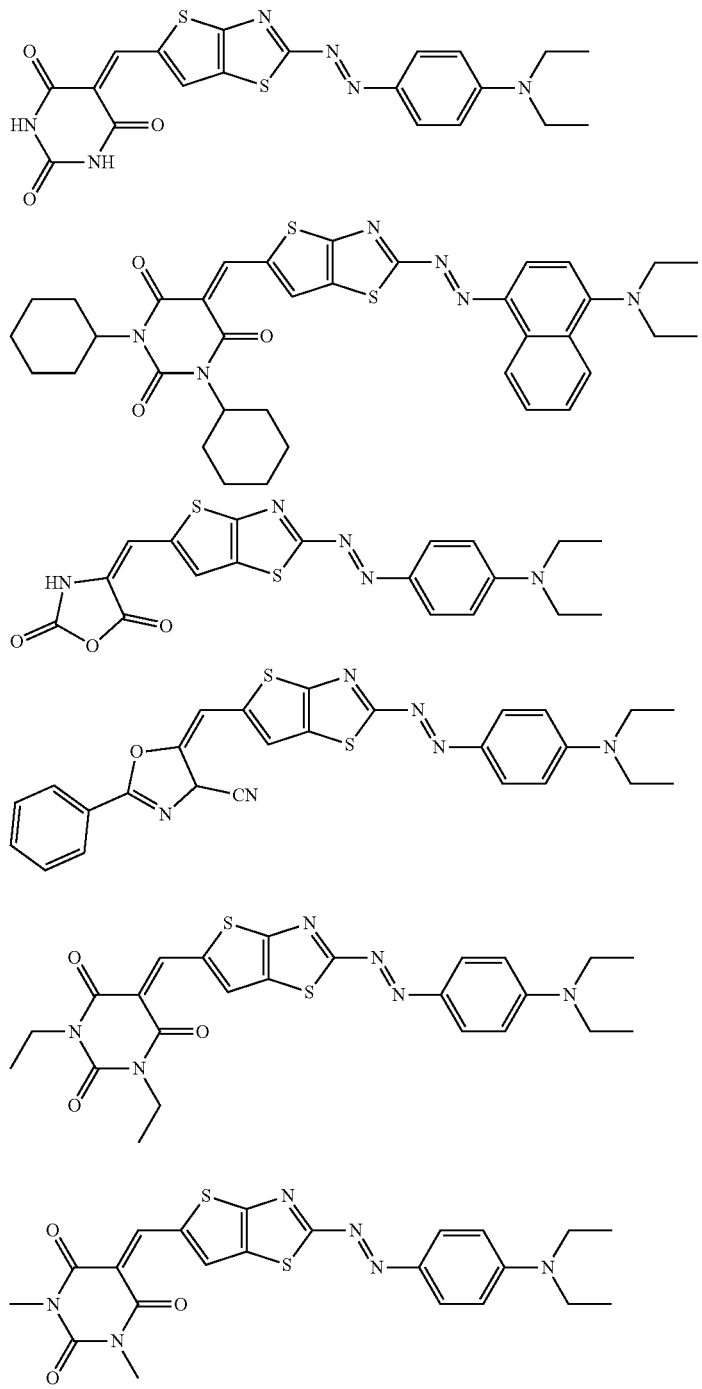

-continued
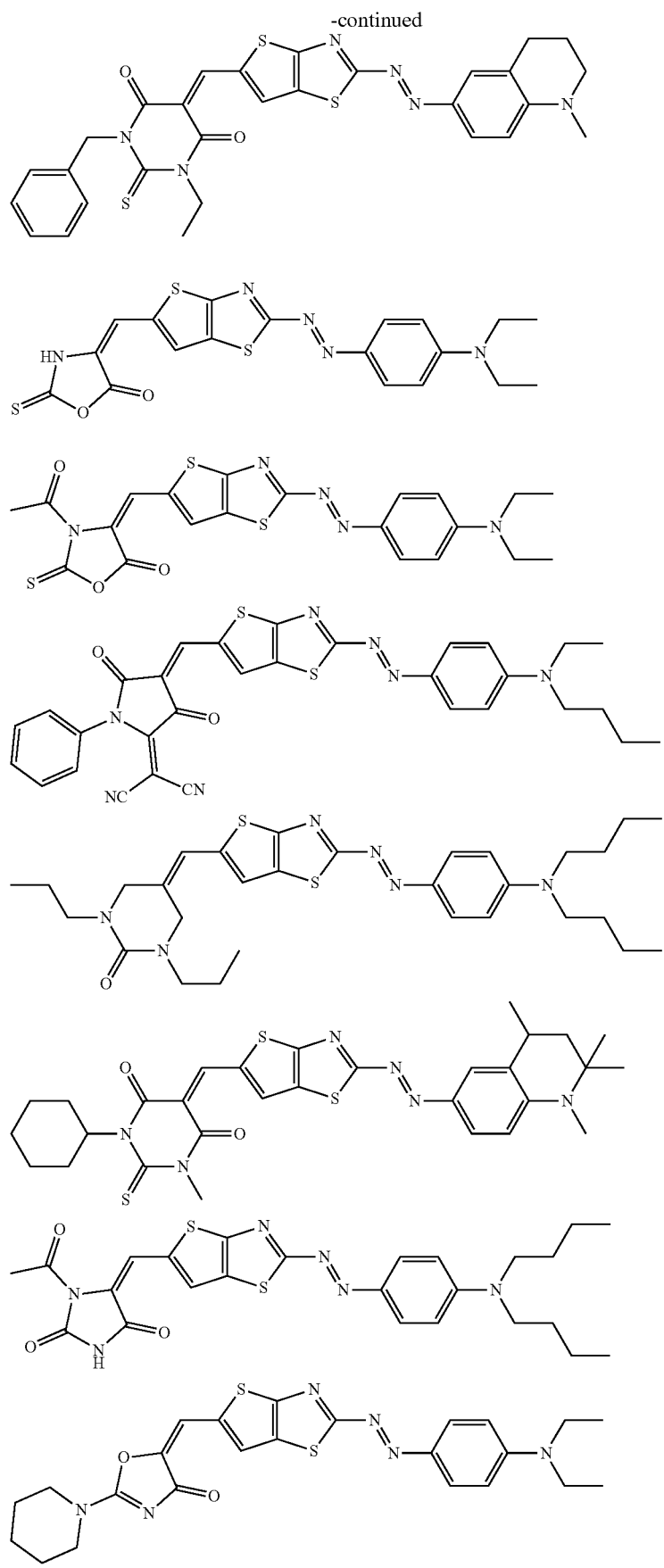

-continued
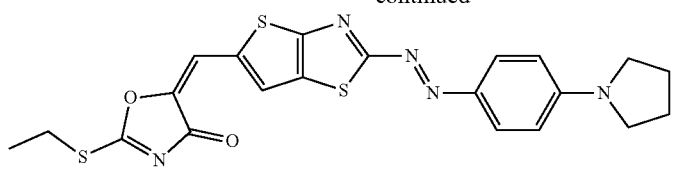
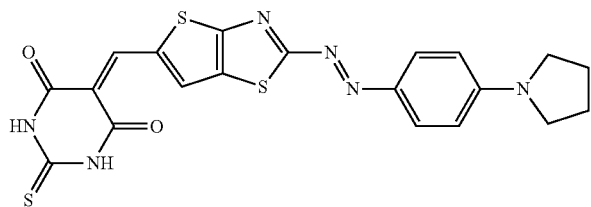
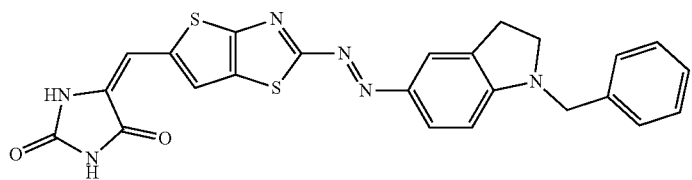
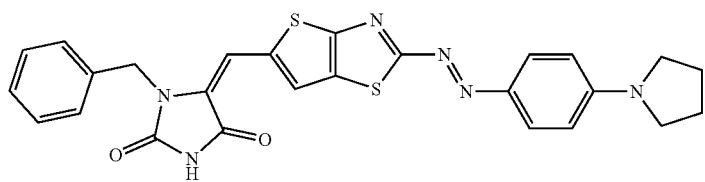
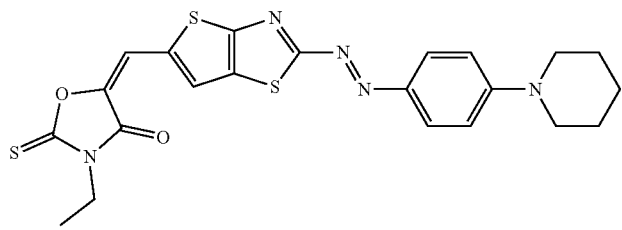
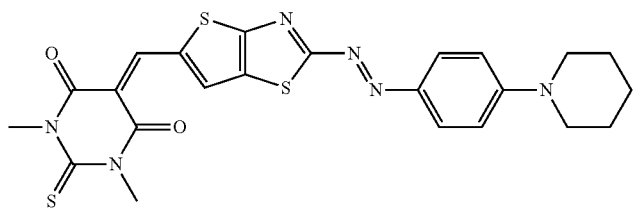
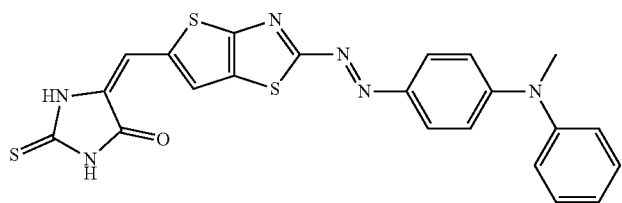
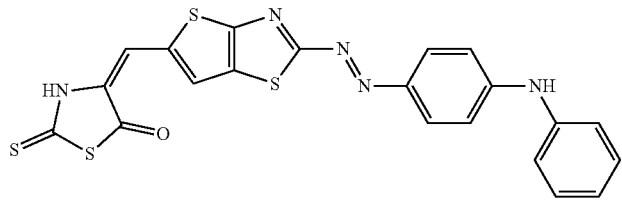

-continued
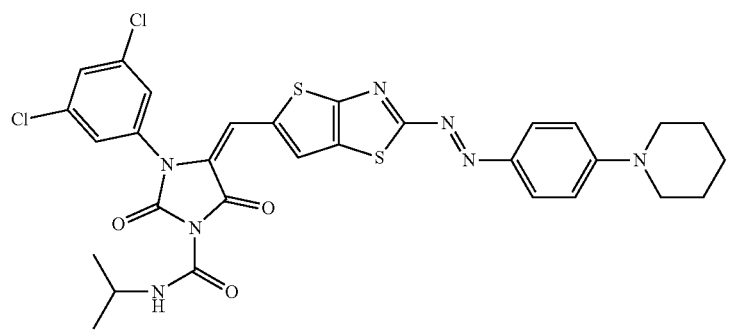
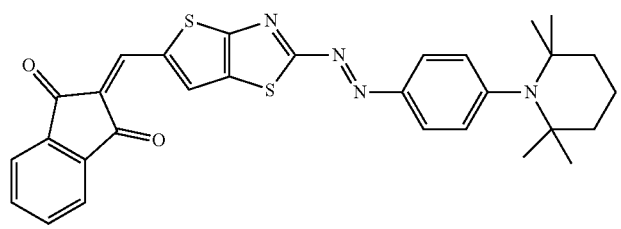
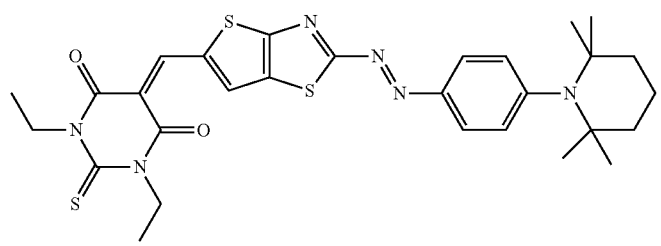
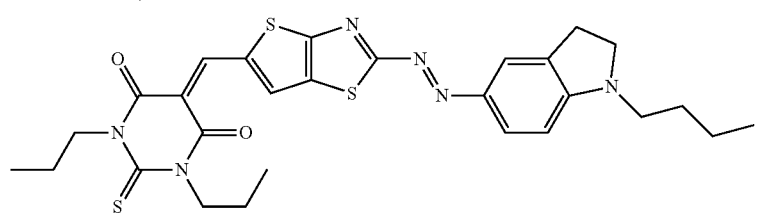
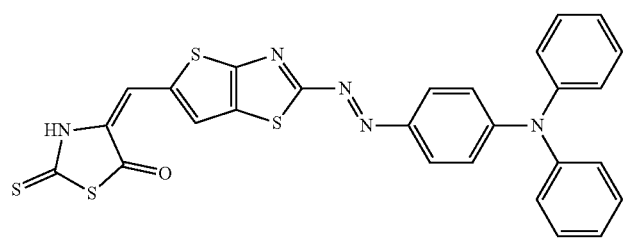
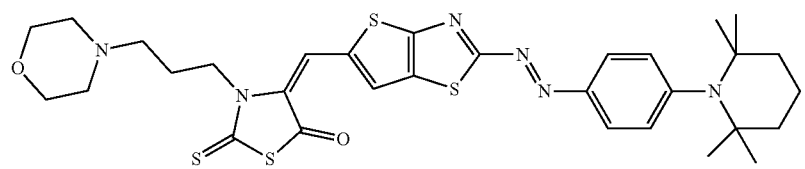
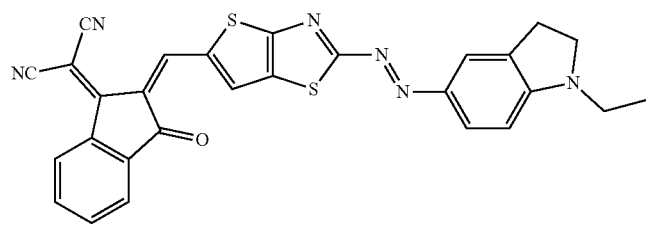

-continued
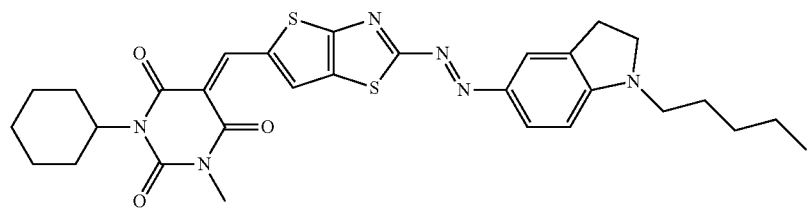
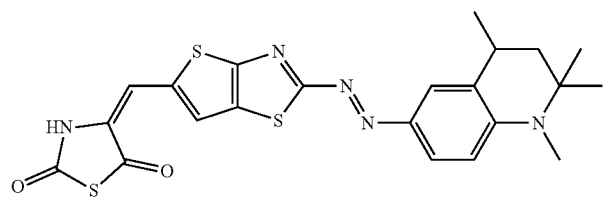
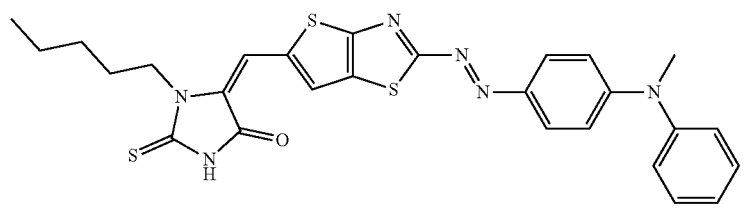
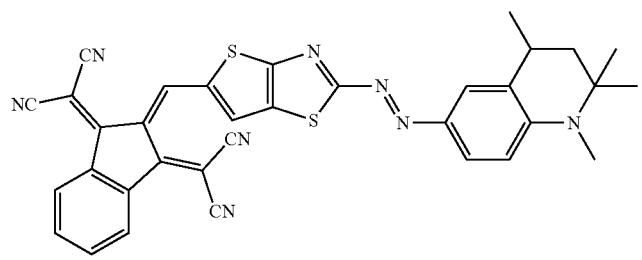
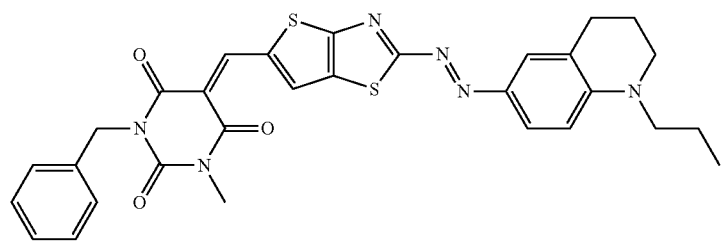
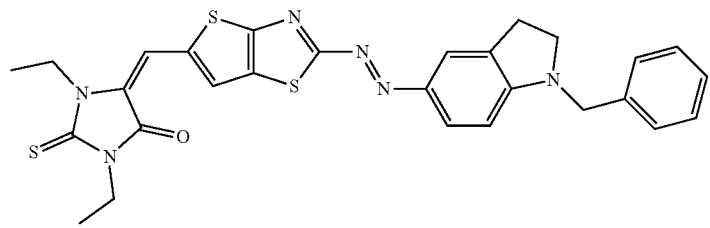
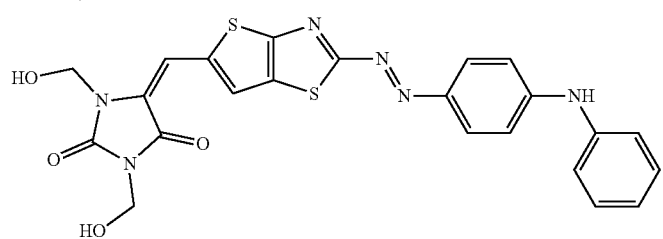

-continued
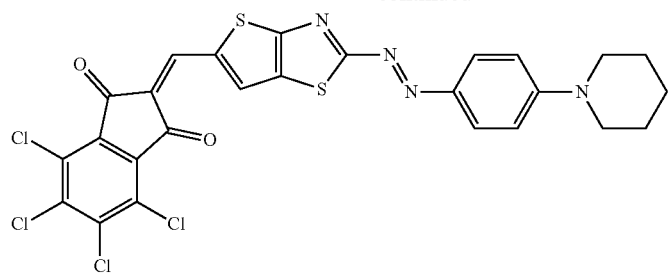
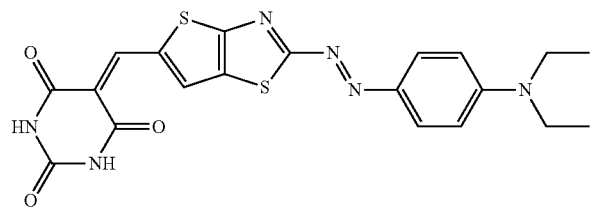
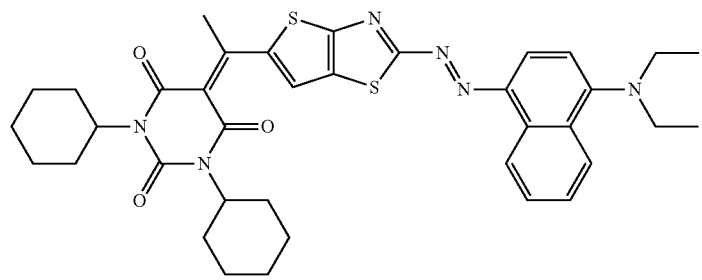
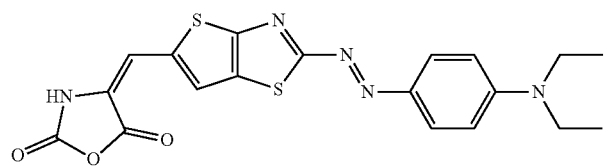
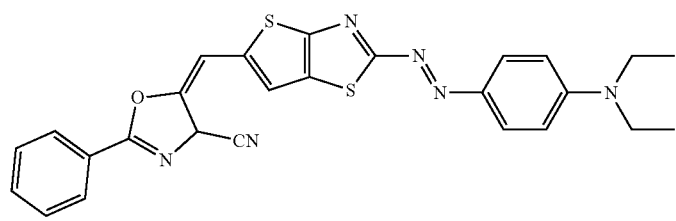
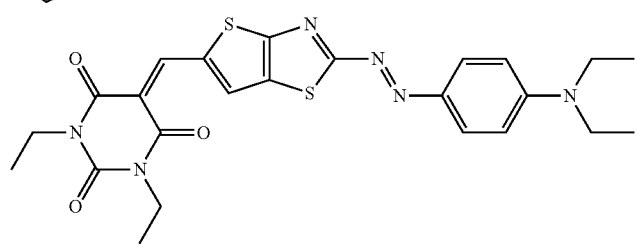
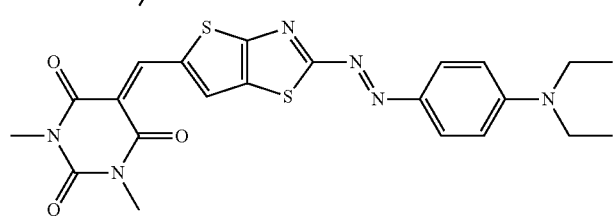

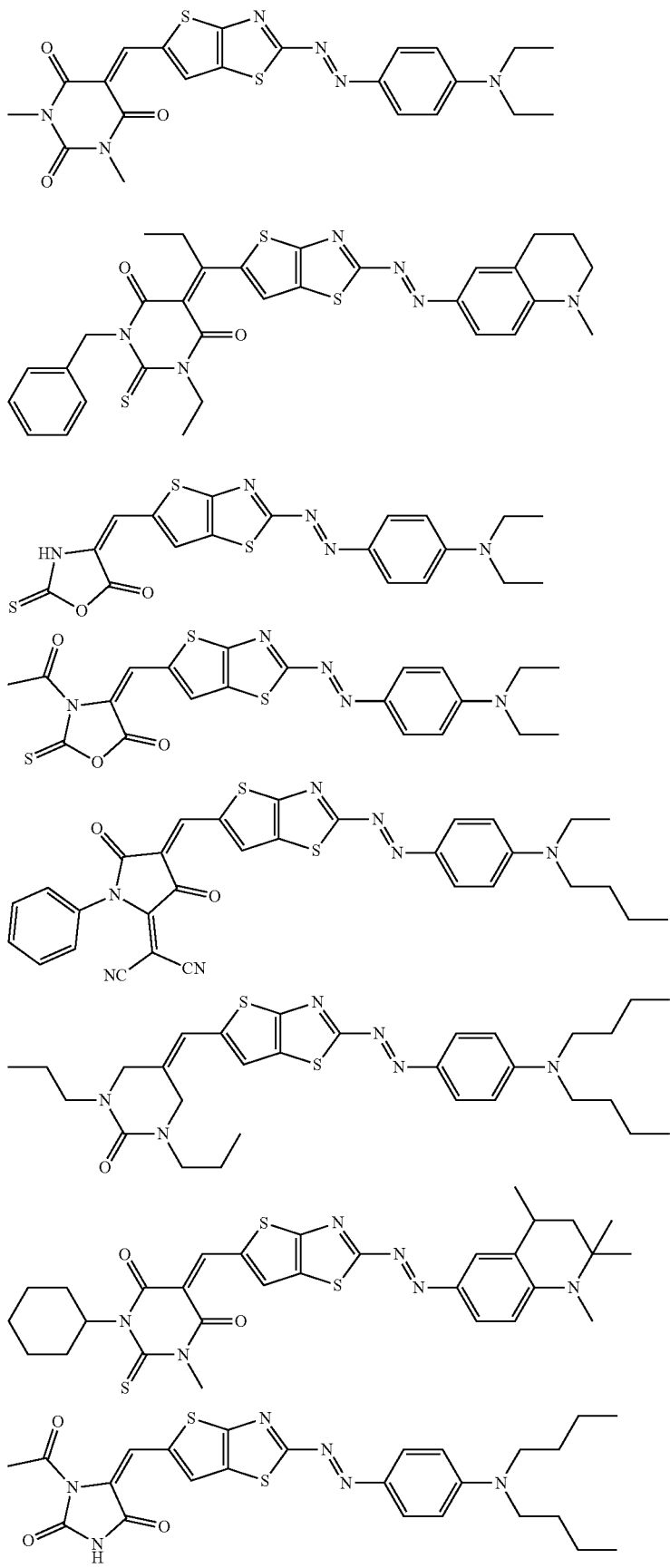

-continued
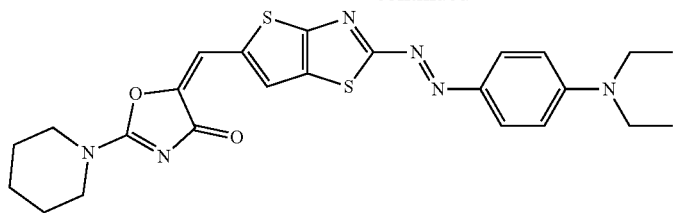
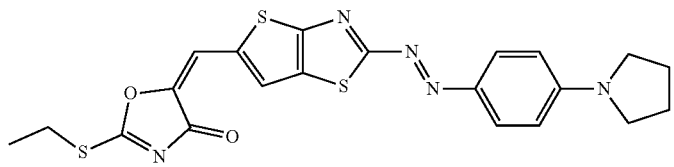
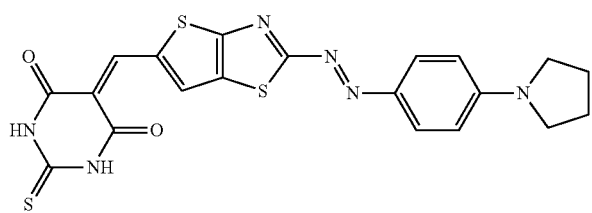
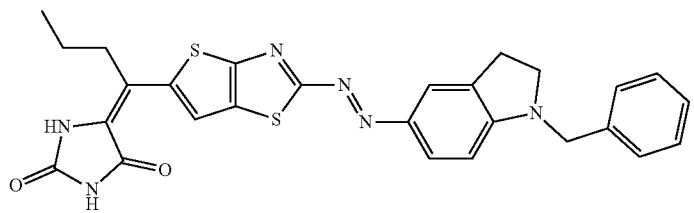
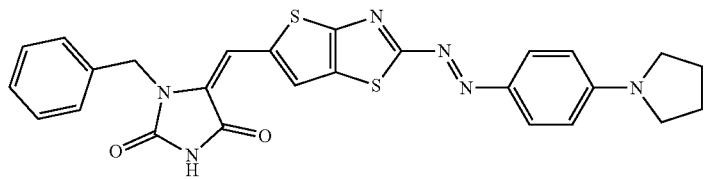
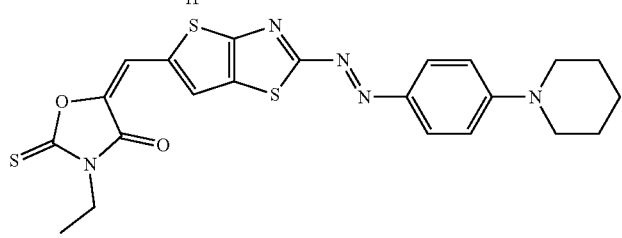
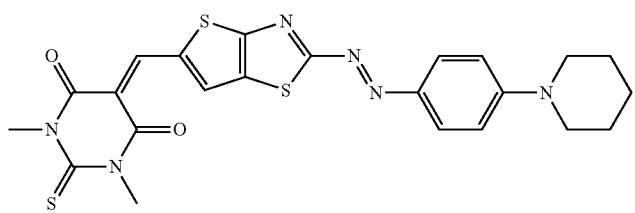
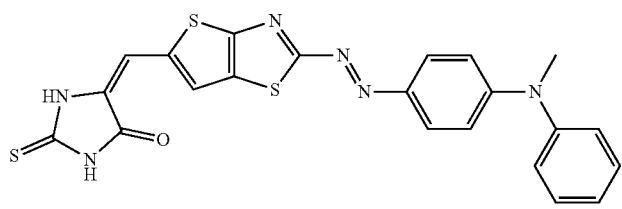

-continued
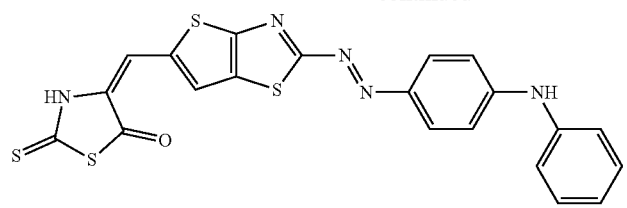
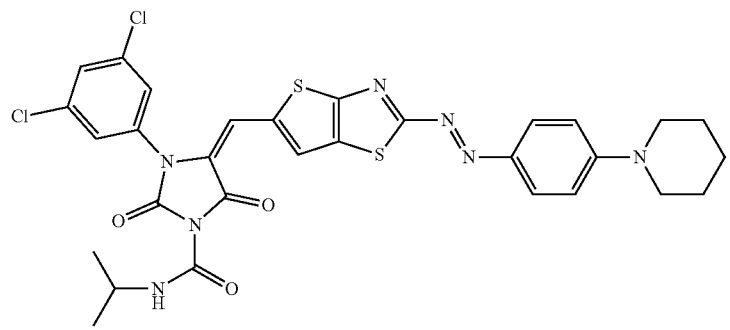
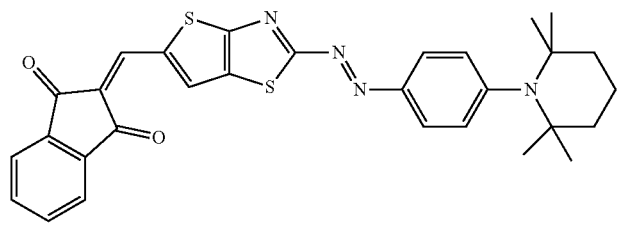
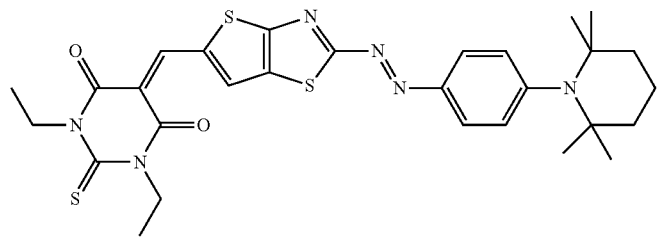
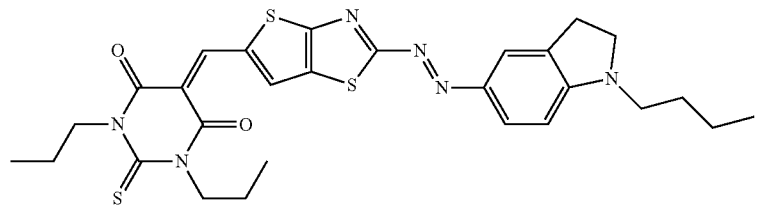
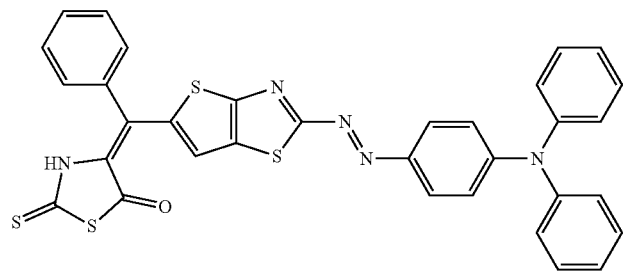
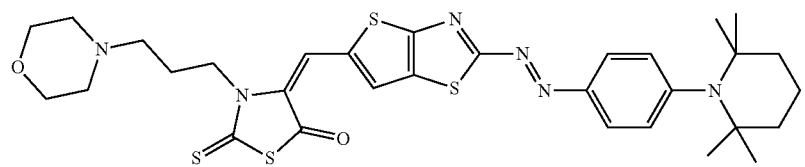

-continued
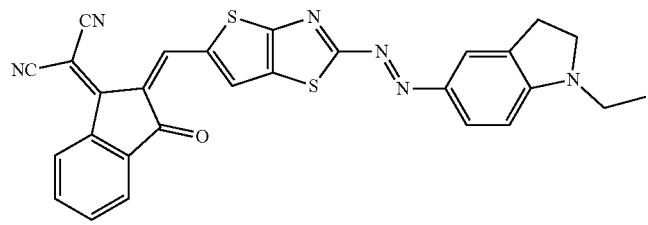
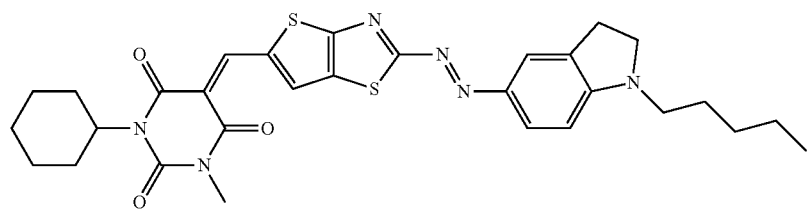
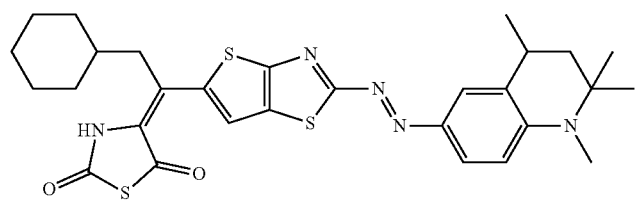
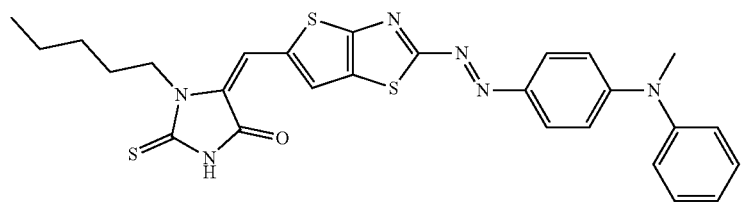
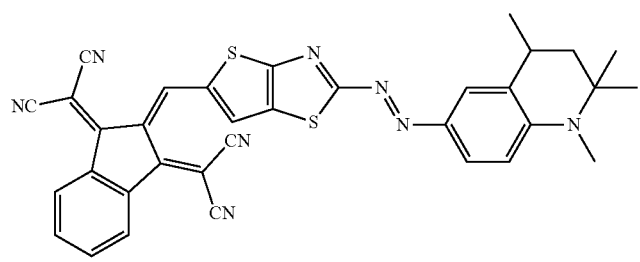
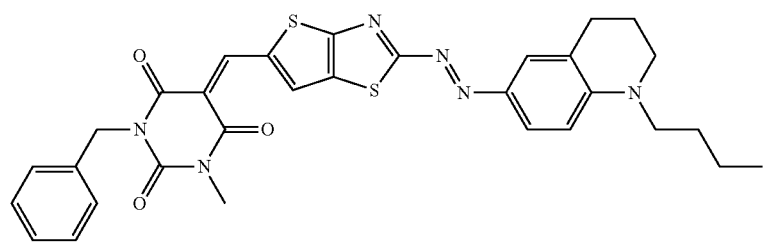
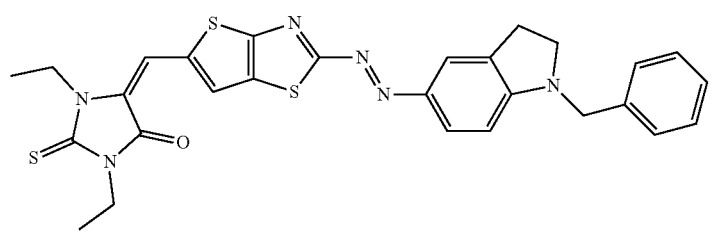

-continued

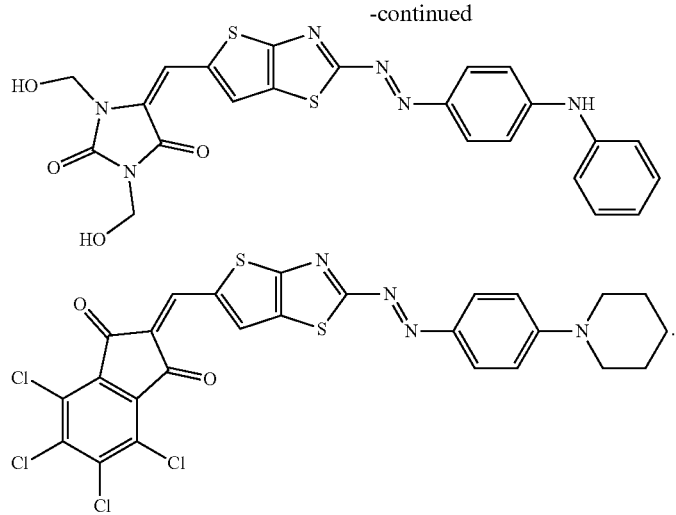

10. A composition for a polarizing plate, comprising:
a liquid crystal compound; and
the mono-azo dichroic dye compound of claim 1.

11. A polarizing plate, which is a cured product of the composition of claim 10.

12. The polarizing plate according to claim 11, wherein the polarizing plate has a dichroic ratio (D0) of 19-25.

13. The polarizing plate according to claim 11, wherein the polarizing plate has a heat resistance (Δ intensity) of 6% or less.

14. The polarizing plate according to claim 11, wherein the polarizing plate has a photo-resistance (Δ intensity) of 3% or less.

15. An optical device comprising the polarizing plate of claim 11.

* * * * *